US006884782B2

(12) United States Patent
Huang et al.

(10) Patent No.: US 6,884,782 B2
(45) Date of Patent: Apr. 26, 2005

(54) STAT MODULATORS

(75) Inventors: Alan Huang, San Mateo, CA (US); Jiwen Liu, Belmont, CA (US); Julio Medina, San Carlos, CA (US); Xuemei Wang, San Bruno, CA (US); Feng Xu, Palo Alto, CA (US); Liusheng Zhu, Burlingame, CA (US)

(73) Assignee: Amgen Inc., Thousand Oaks, CA (US)

( * ) Notice: Subject to any disclaimer, the term of this patent is extended or adjusted under 35 U.S.C. 154(b) by 409 days.

(21) Appl. No.: 10/008,244

(22) Filed: Nov. 7, 2001

(65) Prior Publication Data

US 2002/0151504 A1 Oct. 17, 2002

Related U.S. Application Data

(60) Provisional application No. 60/246,876, filed on Nov. 8, 2000.

(51) Int. Cl.[7] .................................................. C07K 5/06

(52) U.S. Cl. .......................... 514/19; 549/200; 548/535

(58) Field of Search ........................... 514/19; 549/200; 548/535

(56) References Cited

U.S. PATENT DOCUMENTS

| | | | |
|---|---|---|---|
| 5,591,825 A | 1/1997 | McKnight et al. | |
| 5,618,693 A | 4/1997 | McKnight et al. | 435/69.1 |
| 5,639,858 A | 6/1997 | Hoey et al. | |
| 5,710,266 A | 1/1998 | McKnight et al. | |
| 5,716,622 A | 2/1998 | Darnell, Jr. et al. | |
| 5,731,155 A | 3/1998 | Schreiber et al. | |
| 5,756,700 A | 5/1998 | Hoey et al. | 536/23.5 |
| 6,207,391 B1 | 3/2001 | Wu et al. | 435/7.1 |
| 6,426,331 B1 | 7/2002 | McKinney et al. | |

FOREIGN PATENT DOCUMENTS

| | | |
|---|---|---|
| WO | WO 97/05162 A1 | 2/1997 |
| WO | WO 98/31704 A1 | 7/1998 |
| WO | WO 99/24442 A1 | 5/1999 |
| WO | WO 99/50283 A1 | 10/1999 |
| WO | WO 00/027802 A1 | 5/2000 |
| WO | WO 01/83517 A1 | 11/2001 |

OTHER PUBLICATIONS

English Abstract of JP 10175964, issued Jun. 30, 1998 to Sumitomo Seiyaku KK.

English Abstract of JP 10175965, issued Jun. 30, 1998 to Sumitomo Seiyaku KK.

English Abstract of JP 11106340, issued Apr. 20, 1999 to Sumitomo Seiyaku KK.

English Abstract of JP 11116481, issued Apr. 27, 1999 to Sumitomo Seiyaku KK.

English Abstract of JP 2000 229959 A1, issued Aug. 22, 2000 to Sumitomo Chem. Co. Ltd.

Corry et al., J. Exp. Med., 183:109–117 (1996).

Durbin, J.E.: Cell 84(3):443–50 (1996).

Foster, P.S.: Clin. Experimental Allergy 29(1):12–16 (1999).

Henderson: J. Immunol. 164:1086–95 (2000).

Kuperman: J Exp. Med. 187:939 (1998).

Mattes et al., J. Immunol., 167:1683–92 (2001).

Mikita: J. Biol.Chem. 273:17634 (1998).

Oshima and Puri, FASEB Journal 15(6):122–144 (2001).

Perez–G. et al., J. Immunol., 168:1428–34 (2002).

Tomkinson, A.: Am. J. Resp. Crit. Care Med. 160(4):1283–91 (1999).

Trifilieff, A.: Br. J. Pharmacol. 130(7):1581–8 (2000).

Wang, L.H.: Blood 95(4):1249–57 (2000).

Anonymous, “STAT antibodies” Research Diagnostics, pp. 1–9, Mar. 26, 1998.

Anonymous, “Stat sampler kit” The 1998 Online Antibody Catalog, Transduction Laboratories, 5 pages Mar. 29, 1998.

Anonymous, “The jak–STAT mechanism of signal transduction” The Cytokine Bulletin pp. 1–6 (1995) at ≦http://www.mdsystems.com/asp/b≧ (visited on Jan. 8, 2003).

Blommers et al., “Transferred cross–correlated relaxation complements transferred NOE: Structureof an IL–4R–derived peptide bound to STAT–6” J. Am. Chem. Soc. 121(9):1949–1953 (1999).

Carpenter, “Receptor tyrosine kinase substrate: src homology domains and signal transduction” FASEB J. 6:3283–3289 (1992).

Darnell et al., “Jak–Stat pathways and transcriptional activation in response to IFNs and other extracellular signalling proteins” Science 264:1415 (1994).

Hou et al., “An Interleukin–4–induced transcription factor: IL–4 stat” Science 265:1701–1706 (1994).

Ihle et al., “Signaling by the cytokine receptor superfamily: JAKs and STATs” Trends Biochem Sci. 19:222–227 (1994).

Ihle et al., “Jaks and Stats in signaling by the cytokine receptor superfamily” Trends Genetics 11:69–74 (1995).

Kaplan et al., “Impaired IL–12 responses and enhanced development of Th2 cells in stat4–deficient mice” Nature 382:174–177 (1996).

Kaplan, M. et al., “Sta6 is required for mediating responses to IL–4 and for the development of TH2 cells” Immunity 4:313–319 (1998).

Martin, et al., “Sulfonic acid enkephalin: Binding specificity to rat brain opiate receptors” Neuropeptides 6:293–302 (1985).

(Continued)

*Primary Examiner*—Jon Weber
*Assistant Examiner*—David Lukton
(74) *Attorney, Agent, or Firm*—Townsend and Townsend and Crew LLP

(57) ABSTRACT

The present invention provides compounds, compositions and methods for the inhibition or treatment of conditions or disorders modulated by the STAT transcription factors, particularly STAT4 and STAT6. Additionally, the compounds are useful for the diagnosis of conditions dependent on STAT signaling.

102 Claims, 4 Drawing Sheets

OTHER PUBLICATIONS

Myers et al., "The IRS–1 signaling system" Trends in Biochem. Sci. 19:289–293 (1994).

Oshima et al., "A novel interleukin–13 antagonist that blocks the biological activity of human interleukin–13 in immune and nonimmune cells" FASEB Journal 15(6):122–144 (2001).

Pawson, T. "Protein modules and signaling networks" Nature 373:573–580 (1995).

Quelle et al., "Cloning of murine Stat6 and Human Stat6, Stat proteins that are tyrosine phosphorylated in responses to IL–4 and IL–3 but are not required for mitogenesis" Mol. Cell. Biol. 15:336–3343 (1995).

Ryan, J. et al. "Growth and gene expression are predominantly controlled by distinct regions of the human IL–4 receptor" Immunity 4:123–132 (1996).

Schindler, C. et al., "Transcriptional responses to polypeptide ligands: The JAK–STAT pathway" Annu. Rev. Biochem. 64:621–51 (1995).

Schlessinger, J. "SH2/SH3 signaling proteins" Curr. Opin. In. Gen. and Dev. 4:25–30 (1994).

Shuai et al., "Polypeptide signaling to the nucleus through tyrosine phosphorylation of Jak and Stat proteins" Nature 366:580–583 (1993).

Thierfelder et al., "Requirement for stat4 in interleukin–12 mediated responses of natural killer and T cells" Nature 382:171–174 (1996).

Wang, H. et al., "IL–4 function can be transferred to the IL–2 receptor by tyrosine containing sequences found in the IL–4 receptor alpha chain" Immunity 4:113–131 (1996).

Yamamoto et al., "cDNA cloning, expression and chromosome mapping of the human STAT4 gene: both STAT4 and STAT1 genes are mapped to 2q32.2→q32.3" Cytogenet Cell Genet. 77:207–210 (1997).

Yao et al., "Direct interaction of STAT4 with the IL–12 receptor" Archives of Biochemistry and Biophysics 368(1):147–155 (1999).

Zhong et al., "Stat3 and Stat4: Members of the family of signal transducers and activators of transcription" Proc. Natl. Acad. Sci. USA 91:4806–4810 (1994).

ii iii iv v vi vii xi xii xiii xiv vi xv $R^1$ and $R^2$ are each independently lower alkyl.

STAT MODULATORS

CROSS REFERENCE TO REALTED APPLICATIONS

This application claims priority to U.S. Provisional Patent Application No. 60/246,876, filed Nov. 8, 2000, which is incorporated herein by reference in its entirety for all purposes.

FIELD OF THE INVENTION

The present invention relates generally, to novel compounds and pharmaceutical compositions and, more particularly, to STAT inhibitors, such as STAT6 inhibitors and their use as modulators of the immune system.

BACKGROUND OF THE INVENTION

New therapeutic and diagnostic agents have begun to emerge from discovery efforts, which use high-throughput screening directed to certain gene-specific transcription factors.

One family of transcription factors responsible for transmitting a signal to a cell's nucleus are the proteins known as *Signal Transducers and Activators of Transcription* (STATs; see: Darnell et al. (1994) *Science* 264: 1415; for review, see: e.g., Ihle et al. (1994) *Trends Biochem. Sci.* 19: 222; Ihle et al. (1995) Trends Genetics 11: 69); and Horvath et al. (1997) *Curr Opn Cell Biol.* 9:233). STATs are activated by contact with the phosphorylated cytokine receptor; activation results in the STAT polypeptides forming a dimer and entering the nucleus, where the STAT dimer binds to the regulatory region of a gene that is inducible by the particular cytokine. Binding of the activated STAT dimer triggers transcription of the gene.

The STAT polypeptides (STAT1, STAT2, STAT4, STAT5a, STAT5b, and STAT6) have molecular masses from 84–113 kDa. Each STAT protein contains a Src homology-2 (SH2) domain capable of recognizing one or more phosphotyrosine sequences in the cytoplasmic portion of the activated receptor (see, Shuai et al. (1993) *Nature* 366: 580). Additionally, each cytokine receptor is specific for a particular STAT protein, and each STAT activates transcription of certain genes, thereby providing two layers of specificity in cytokine-induced signalling.

STAT6 and STAT4 are two proteins that are intimately involved in regulation of immune responses. STAT4 transduces to the nucleus signals from the IL-12 receptor. IL-12 is involved in the development of a $T_H1$ immune response (see, Kaplan et al. (1996) *Nature* 382: 174–177), which is part of an organism's defense against intracellular pathogens. IL-12 is also necessary for the T-cell-independent induction of the cytokine interferon (IFN)-γ, which is a key step in the initial suppression of bacterial and parasitic infections. Knockout mice which lack STAT4 were found to be defective in all IL-12 functions tested, including the induction of IFN-gamma, mitogenesis, enhancement of natural killer cytolytic function and $T_H1$ differentiation (see, Thierfelder et al. (1996) *Nature* 382: 171–174).

IL-4 signals are transduced to the nucleus by STAT6. In addition, IL-4 is a key cytokine in the initiation of a $T_H2$ immune response, and also activates B and T lymphocytes. STAT6-deficient mice were shown to be deficient in IL-4 activities (see, Kaplan et al. (1996) *Immunity* 4: 313–319; Takeda et al. (1996) *Nature* 380: 627–630; Shimoda et al. (1996) *Nature* 380: 630–633).

Because of the importance of STAT4 and STAT6 in modulating the immune response of an organism, both in response to infection and in undesirable conditions such as inflammation, allergic reactions, and autoimmune diseases, a need exists by which the clinician can diagnose, enhance or reduce STAT4 and STAT6 signals. Intervention at the STAT level would have significant advantages compared to previous approaches, which typically target the IL-4 or IL-12 cytokine itself, or the interaction of the cytokine with the receptor. Disruption of cytokine function itself can cause a variety of undesirable side effects. These can be avoided by intervening at the level of STAT-mediated signal transduction.

WO 98/40478, published Sep. 17, 1998, discloses an oligonucleotide having 10 to 30 nucleotide units which is complementary to at least part of mRNA encoding human Stat-6 and is capable of inhibiting expression of Stat-6.

Identification of agents that can modulate STAT4 and STAT6-mediated signal transduction has heretofore been hampered by the lack of suitable assays. Recently, a new assay for identification of STAT6 and STAT4 signalling modulators was described (see, U.S. Pat. No. 6,207,391). Assay of binding of STAT4 and STAT6 to their corresponding receptors, and identification of agents which increase or decrease the degree of such binding, has now led to the identification of compounds which are useful in the diagnosis and treatment of various STAT-dependent conditions.

U.S. patent application Ser. No. 09/349,208, filed Jul. 7, 1999, and incorporated herein by reference, discloses STAT protein modulators useful for a variety of indications. Despite the advances made by the U.S. patent application Ser. No. 09/349,208, there remains a need for novel compounds capable of modulated STAT proteins such as STAT6. The present invention fulfills this and other needs.

SUMMARY OF THE INVENTION

The present invention provides compounds, compositions and methods for the inhibition or treatment of conditions or disorders modulated by the STAT transcription factors, particularly STAT6. As such, in certain aspects, the present invention provides compounds of Formula I:

I

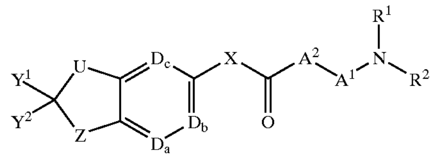

In the above formula, $R^1$ and $R^2$ are each independently selected from hydrogen, $(C_1–C_8)$alkyl, $(C_1–C_8)$heteroalkyl, aryl, aryl$(C_1–C_8)$alkyl, aryl$(C_1–C_8)$heteroalkyl, heteroaryl, heteroaryl$(C_1–C_8)$alkyl, and heteroaryl$(C_1–C_8)$heteroalkyl, with the proviso that at least one of $R^1$ and $R^2$ is selected from aryl, aryl$(C_1–C_8)$alkyl, aryl$(C_1–C_8)$heteroalkyl, heteroaryl, heteroaryl$(C_1–C_8)$alkyl and heteroaryl$(C_1–C_8)$heteroalkyl.

The symbol $A^1$ represents a divalent L-α-amino acid or D-α-amino acid fragment or a fragment having the formula:

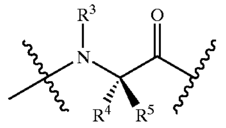

in which $R^3$ is hydrogen or $(C_1–C_4)$alkyl, and $R^4$ and $R^5$ are each independently selected from hydrogen, $(C_1–C_8)$alkyl and $(C_1–C_8)$heteroalkyl, or $R^4$ and $R^5$ can be individually combined with $R^3$ to form a 5-, 6-, 7- or 8-membered ring containing from one to three heteroatoms.

The symbol $A^2$ represents an L-α-amino acid or D-α-amino acid fragment or a fragment having the formula:

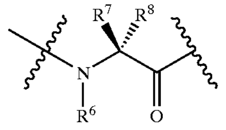

In the indicated formula, $R^6$ is either hydrogen or $(C_1–C_4)$ alkyl; $R^7$ and $R^8$ are independently selected from hydrogen, $(C_1–C_8)$alkyl and $(C_1–C_8)$heteroalkyl, or $R^7$ and $R^8$ can be combined with each other to form a 5-, 6-, 7- or 8-membered ring containing from zero to three heteroatoms. For each of the $A^1$ and $A^2$ groups above, the wavy line is meant to indicate the point of attachment to the remainder of the molecule. The amino acid fragments are those portions of an amino acid that remain after removal of the OH group from the carboxylic acid portion and a hydrogen atom from the α-amino portion.

The letter X represents a bond, a $(C_1–C_4)$ saturated or unsaturated alkyl linking group or a $(C_1–C_4)$ saturated or unsaturated heteroalkyl linking group.

The symbols $D_a$, $D_b$ and $D_c$ each independently represent a divalent radical selected from =N— and =C($R^9$)—, in which each $R^9$ is independently selected from hydrogen, halogen, cyano, nitro, $(C_1–C_6)$alkyl, $(C_1–C_6)$heteroalkyl, $(C_1–C_6)$alkoxy, $(C_1–C_6)$thioalkoxy, —O—C(O)—$NR^{10}R^{11}$, —$NR^{10}R^{11}$, —C(O)$OR^{10}$, —C(O)$NR^{10}R^{11}$, —O—C(O)$OR^{10}$, —$NR^{11}$—C(O)$OR^{10}$, —$NR^{10}$—$SO_2R^{12}$, —$NR^{10}$—C(O)$R^{11}$, —$SO_2NR^{10}R^{11}$, and —OC(O)$NR^{10}R^{11}$; in which $R^{10}$ and $R^{11}$ are each independently selected from hydrogen, $(C_1–C_8)$alkyl and $(C_1–C_8)$heteroalkyl. In an alternative embodiment, when $R^{10}$ and $R^{11}$ are attached to the same nitrogen atom they can be combined with each other to form a 5, 6-, 7- or 8-membered ring containing from zero to three heteroatoms and each $R^{12}$ is independently selected from $(C_1–C_8)$alkyl, $(C_1–C_8)$heteroalkyl, aryl and heteroaryl.

The letters U and Z each independently represents a single bond, —$CH_2$—, —CH(OH)—, —C(O)—, —$CH_2O$—, —$CH_2CH_2$—, —$CH_2C(O)$—, —O—, —S—, —S—$CH_2$—, —N(C(O)—$(C_1–C_9)$alkyl)-, —N($R^{13}$)— and —N($R^{13}$)—$CH_2$—, in which each $R^{13}$ is selected from hydrogen, $(C_1–C_8)$alkyl, aryl and $(C_1–C_8)$heteroalkyl;

In the above formula, $Y^1$ and $Y^2$ each independently represent —$CO_2H$ or —$CO_2R^{14}$, in which $R^{14}$ is selected from $(C_1–C_9)$alkyl, and $(C_1–C_9)$heteroalkyl. In an alternative embodiment, when $Y^1$ and $Y^2$ are each —$CO_2R^{14}$, each $R^{14}$, and the oxygen to which it is attached, can join to form a 5-, 6-, 7- or 8-membered heterocyclic ring.

The compounds of the present invention are useful in compositions that further comprise a pharmaceutically acceptable excipient. Both the compounds and compositions of the present inventions are useful for the diagnosis and treatment (including prophylactic treatment) of conditions mediated through STAT signaling. Examples of conditions associated with STAT signaling include, but are not limited to, $T_H1$-mediated conditions such as delayed-type hypersensitivity, contact dermatitis, uveitis, Crohn's disease, psoriasis and autoimmune diseases (typically associated with STAT4 signaling); $T_H2$ mediated diseases such as allergic rhinitis, asthma, scleroderma, eczema and conjunctivitis (typically associated with STAT6 signaling); proliferative disorders such as cancers (associated with STAT3 and/or STAT5 signaling); and STAT1 conditions which are similar to those described for STAT4, but typically observed in more acute situations such as acute transplant rejections. A variety of additional conditions associated with STAT signaling include atopic dermatitis, anaphylaxis, food or drug induced allergy, hypersensitivity reactions, alveolitis, Churg-Strauss syndrome, urticaria, angiodema, and systemic lupus erythematosus.

Other objects, features and advantages of the present invention will be apparent to one of skill in the art from the following detailed description and the claims.

DETAILED DESCRIPTION OF THE INVENTION AND PREFERRED EMBODIMENTS

Abbreviations

Figure 1:
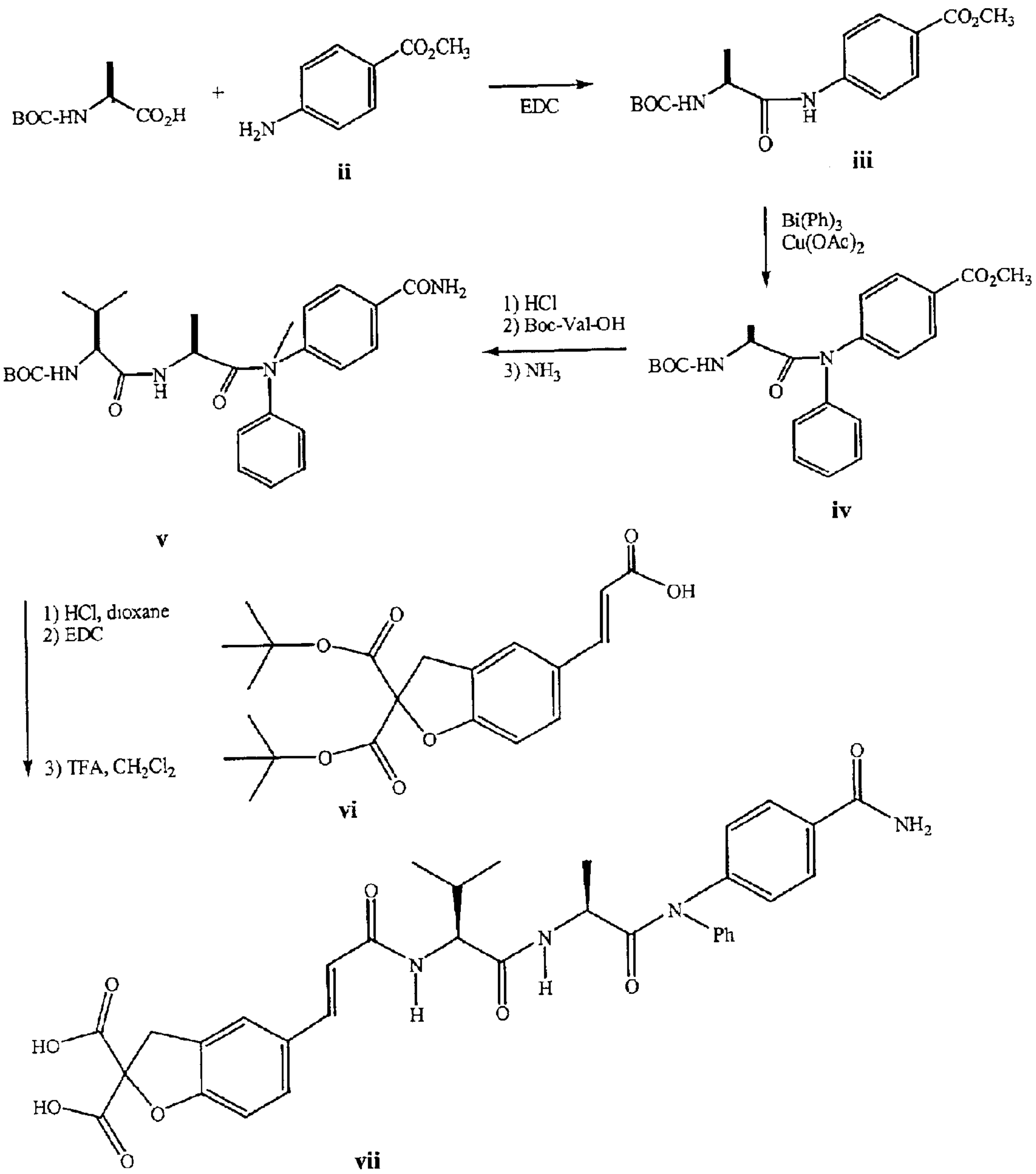
FIG. 1 illustrates a synthetic scheme to a particular embodiment of the present invention.

The following abbreviations are used herein: Ac, acetyl; Bn, benzyl; Bz, benzoyl; Boc, t-butoxycarbonyl; EDC, 1-(3-Dimethylaminopropyl)-3-ethylcarbodiimide hydrochloride; HOBT, hydroxybenzotriazole; NMM, N-methylmorpholine; DMF, dimethylformamide; EtOAc, ethyl acetate; HBTU, 2-(1H-benzotriazole-1-yl)-1,1,3,3-tetramethyluronium hexafluorophosphate; THF, tetrahydrofuran; FMOC, fluorenylmethyloxycarbonyl; TFA, trifluoroacetic acid; Me, methyl; Et, ethyl; Ph, phenyl; STAT, *Signal Transducers and Activators of Transcription*; rt, room temperature.

Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $(C_1–C_{10})$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkylene" by itself or as part of another substituent means a divalent radical derived from an alkane, as exemplified by $—CH_2CH_2CH_2CH_2—$. Typically, an alkyl or alkylene group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2—S(O)—CH_3$, $—CH_2—CH_2—S(O)_2—CH_3$, $—CH=CH—O—CH_3$, $—Si(CH_3)_3$, $—CH_2—CH=N—OCH_3$, and $—CH=CH—N(CH_3)—CH_3$. Up to two heteroatoms may be consecutive, such as, for example, $—CH_2—NH—OCH_3$ and $—CH_2—O—Si(CH_3)_3$. Also included in the term "heteroalkyl" are those radicals described in more detail below as "heterocycloalkyl." The term "heteroalkylene" by itself or as part of another substituent means a divalent radical derived from heteroalkyl, as exemplified by $—CH_2—CH_2—S—CH_2CH_2—$ and $—CH_2—S—CH_2—CH_2—NH—CH_2—$. For heteroalkylene groups, heteroatoms can also occupy either or both of the chain termini. Still further, for alkylene and heteroalkylene linking groups, no orientation of the linking group is implied.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', $—CO_2R'$, CONR'R", —OC(O)NR'R", —NR"C(O)R', —NR'—C(O)NR"R'", $—NR"C(O)_2R'$, $—NH—C(NH_2)=NH$, $—NR'C(NH_2)=NH$, $—NH—C(NH_2)=NR'$, —S(O)R', $—S(O)_2R'$, $—S(O)_2NR'R"$, —CN and $—NO_2$ in a number ranging from zero to (2N+1), where N is the total number of carbon atoms in such radical. R', R" and R'" each independently refer to hydrogen, unsubstituted $(C_1–C_8)$alkyl and heteroalkyl, unsubstituted aryl, aryl substituted with 1–3 halogens, unsubstituted alkyl, alkoxy or thioalkoxy groups, or aryl-$(C_1–C_4)$alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similarly, substituents for the aryl groups are varied and are selected from: -halogen, —OR', —OC(O)R', —NR'R", —SR', —R', —CN, $—NO_2—$ $—CO_2R'$, —CONR'R", —C(O)R', —OC(O)NR'R", —NR"C(O)R', $—NR"C(O)_2R'$, —NR'—C(O)NR"R'", $—NH—C(NH_2)=NH$, $—NR'C(NH_2)=NH$, $—NH—C(NH_2)=NR'$, —S(O)R', $—S(O)_2R'$, $—S(O)_2NR'R"$, $—N_3$, $—CH(Ph)_2$, perfluoro$(C_1–C_4)$alkoxy, and perfluoro$(C_1–C_4)$alkyl, in a number ranging from zero to the total number of open valences on the aromatic ring system; and where R', R" and R'" are independently selected from hydrogen, $(C_1–C_8)$alkyl and heteroalkyl, unsubstituted aryl, (unsubstituted aryl)-$(C_1–C_4)$alkyl, and (unsubstituted aryl)oxy-$(C_1–C_4)$alkyl.

Two of the substituents on adjacent atoms of the aryl ring may optionally be replaced with a substituent of the formula —T—C(O)—$(CH_2)_q$—T'—, wherein T and $T^1$ are independently —NH—, —O—, —$CH_2$— or a single bond, and the subscript q is an integer of from 0 to 2. Alternatively, two of the substituents on adjacent atoms of the aryl ring may optionally be replaced with a substituent of the formula —A—$(CH_2)_r$—B—, wherein A and B are independently —$CH_2$—, —O—, —NH—, —S—, —S(O)—, —$S(O)_2$—, —$S(O)_2NR'$— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2NR'$— is selected from hydrogen or unsubstituted $(C_1$–$C_6)$alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical *Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Still further, the compounds of the present invention can be conjugated to easily-detectable groups, such as fluorescein or biotin, for use as reagents or diagnostic tools. Additionally, such tagged compounds can be further attached to a solid support (e.g., bead, resin or microtiter plate)and used in binding experiments to discover other compounds that interact with STAT6.

General

The present invention provides compounds, compositions and methods for the inhibition or treatment of conditions or disorders modulated by the STAT transcription factors, particularly STAT4 and STAT6. Additionally, the compounds are useful for the diagnosis of conditions dependent on STAT signaling. Without intending to be bound by a theory, it is believed that certain compounds of the present invention block interaction between phosphorylated tyrosine residues in the IL-4 receptor and the SH2 domain of STAT6. In this manner, phosphorylation (i.e., activation) of STAT6 by IL-4-receptor-associated kinases is prevented. It is also believed that the compounds exert their effect by interfering with the dimerization of STAT6 monomers that is required before the STAT6 dimer can bind to the STAT6-dependent genes and initiate transcription of, for example, germline epsilon transcript. In view of this transcriptional control, the compounds, compositions and methods of the present invention will be useful in treating (suppressing or inhibiting) the full spectrum of immune disorders which require transcriptional activation by STAT6 dimer, including allergic conditions (e.g., allergic rhinitis, asthma, atopic dermatitis, contact dermatitis, anaphylaxis, food or drug induced allergy, conjunctivitis, uveitis, hypersensitivity reactions, alveolitis and psoriasis), Churg-Strauss syndrome, delayed-type hypersensitivity, urticaria, angiodema, eczema, scleroderma, and systemic lupus erythematosus.

Embodiments of the Invention

Compounds

In one aspect, the present invention provides compounds, which are represented by Formula I:

I

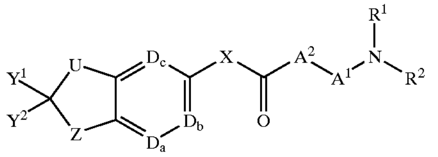

In the above formula, $R^1$ and $R^2$ are each independently selected from hydrogen, $(C_1-C_8)$alkyl, $(C_1-C_8)$heteroalkyl, aryl, aryl$(C_1-C_8)$alkyl, aryl$(C_1-C_8)$heteroalkyl, heteroaryl, heteroaryl$(C_1-C_8)$alkyl, and heteroaryl$(C_1-C_8)$heteroalkyl, with the proviso that at least one of $R^1$ and $R^2$ is selected from aryl, aryl$(C_1-C_8)$alkyl, aryl$(C_1-C_8)$heteroalkyl, heteroaryl, heteroaryl$(C_1-C_8)$alkyl and heteroaryl$(C_1-C_8)$ heteroalkyl.

In one group of embodiments, $R^1$ is selected from $(C_1-C_8)$alkyl and $(C_1-C_8)$heteroalkyl, and $R^2$ is selected from aryl, aryl$(C_1-C_8)$alkyl, and aryl$(C_1-C_8)$heteroalkyl. More preferably, $R^2$ is selected from aryl and aryl$(C_1-C_8)$ alkyl. Still more preferably, $R^1$ is selected from $(C_1-C_4)$ alkyl and $R^2$ is substituted or unsubstituted aryl. Most preferred are those embodiments in which $R^2$ is an optionally substituted phenyl or optionally substituted benzyl group.

In another group of embodiments, $R^1$ and $R^2$ are each selected from aryl, aryl$(C_1-C_8)$alkyl and aryl$(C_1-C_8)$ heteroalkyl. In one group of particularly preferred embodiments, $R^1$ and $R^2$ are each independently an optionally substituted phenyl group. In still other preferred embodiments, $R^1$ and $R^2$ are both optionally substituted benzyl groups. In yet other preferred embodiments, $R^1$ is an optionally substituted phenyl group and $R^2$ is an optionally substituted benzyl group. With the embodiments described herein, the substituents on the aryl rings can be any of those substituents described above in the definitions section. Preferably, however, the substituents are selected from $—CONH_2$, $—CH_2NHCO$-(4-nitro-2-pyrazolyl), $—NHCONH_2$, —C(NH)$NH_2$, —CONHPh, $—CH_2NH_2$, $—CH_2NHCO—CH{=}CH$-(3-nitrophenyl), $—CH_3$, —Cl, —Br, —I, $—CO_2H$, $—CO_2CH_3$, $—OCH_3$, —OH, —Ph, —OPh, $—CON(CH_3)_2$, $—C(CH_3)_3$, $—CH_2NHAc$, —CN, $—CH_2NHCO—CH{=}CH$-(4-pyridyl), and the like. In certain preferred embodiments, $R^1$ and $R^2$ are phenyl or benzyl groups and the additional substituents occupy positions on the benzene ring that are meta or para to the positions at which the benzene rings are attached to the remainder of the molecule.

In formula (I), the symbol $A^1$ represents a divalent L-α-amino acid or D-α-amino acid fragment or a fragment having the formula:

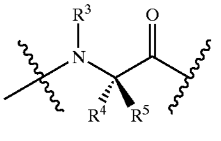

in which $R^3$ is hydrogen or $(C_1-C_4)$alkyl, and $R^4$ and $R^5$ are each independently selected from hydrogen, $(C_1-C_8)$alkyl, or $(C_1-C_8)$heteroalkyl, or $R^4$ and $R^5$ can be individually combined with $R^3$ to form a 5-, 6-, 7- or 8-membered ring containing from one to three heteroatoms. One of skill in the art will understand that when $A^1$ is described as an amino acid or an amino acid fragment, what is meant is a residue of the amino acid that typically remains upon incorporation of the amino acid into a peptide or other similar linear array or polymer. By way of example, if $A^1$ is "alanine," the term is meant to refer to that fragment that is typically incorporated into a peptide or protein (i.e., $—NH—CH(CH_3)—C(O)—$). In certain preferred embodiments, $A^1$ is an amino acid selected from 2-aminoisobutyric acid, sarcosine, norvaline, homoserine, citrulline, norleucine, 2,3-diaminopropionic acid, methionine oxide, methionine dioxide, penicillamine, homoleucine, ornithine, 3H-dehydroproline, 2-methylproline, homoproline, 5-phenylproline, 4-chloroproline, proline, tyrosine, serine, methionine and alanine.

In another group of preferred embodiments, $A^1$ is a fragment having the formula above in which $R^5$ is hydrogen and $R^3$ and $R^4$ are combined to form a 5-, 6-, or 7-membered ring containing from one to three heteroatoms. More preferably, $R^3$ and $R^4$ are combined to form a 5-membered ring containing from one to three heteroatoms. In other preferred embodiments, $A^1$ is a fragment selected from

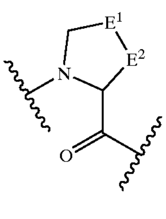 , 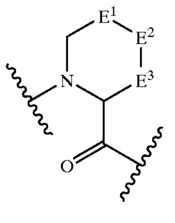 and 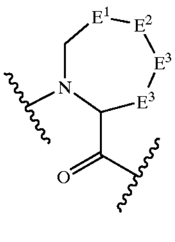

in which $E^1$, $E^2$, $E^3$ and $E^4$ each independently represent C, N, S or O, with the proviso that the 5-, 6- or 7-membered ring contains no more than three heteroatoms as ring members. When any of $E^1$ to $E^4$ are C or N, the remaining valences can be occupied by bonds to hydrogen, aryl, $(C_1-C_8)$alkyl, $(C_1-C_8)$heteroalkyl, aryl$(C_1-C_8)$alkyl, aryl $(C_1-C_8)$heteroalkyl, alkylsulfonyl, arylsulfonyl and arylsulfinyl. Preferably, when any of $E^1$ to $E^4$ are N, the remaining valence is occupied by $(C_1-C_8)$alkyl, most preferably substituted $(C_1-C_8)$alkyl (e.g., acetyl, propionyl and the like).

In one group of particularly preferred embodiments, $A^1$ is represented by the formula:

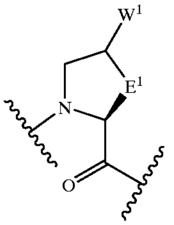

in which $W^1$ represents H, $—OR^{12}$ or $—NR^{12}R^{13}$. The $R^{12}$ and $R^{13}$ groups independently represent hydrogen, aryl, $(C_1-C_8)$alkyl, $(C_1-C_8)$heteroalkyl, aryl$(C_1-C_8)$alkyl, aryl $(C_1-C_8)$heteroalkyl, alkylsulfonyl, arylsulfonyl and arylsulfinyl. Preferably, $W^1$ is $—NHCOCH_3$, $—NHCOCH_2CH_2NHAc$, $—NH_2$, —NH-tosyl, —NHCOPh, $—NHCOCH(CH_3)_2$, $—NHSO_2CH_3$, $—NHCO2_2CH_2Ph$, $—N(CH_3)_2$, and $—N(CH_2Ph)_2$. The $W^1$ group can have either a cis or trans orientation relative to the carbonyl group at the 2-position of the pyrrolidine ring, or can exist as a mixture of isomers at the center bearing the $W^1$ group.

The symbol $A^2$ represents an L-α-amino acid or D-α-amino acid fragment or a fragment having the formula:

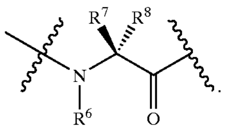

In the indicated formula, $R^6$ is either hydrogen or $(C_1–C_4)$ alkyl; $R^7$ and $R^8$ are independently selected from hydrogen, $(C_1–C_8)$alkyl, $(C_1–C_8)$heteroalkyl, or in an alternative embodiment, $R^7$ and $R^8$ can be combined with each other to form a 5-, 6-, 7- or 8-membered ring containing from zero to three heteroatoms.

In preferred embodiments, $A^2$ represents an amino acid selected from norvaline, homoserine, cyclohexylalanine, norleucine, diaminopropionic acid, methionine oxide, homoleucine, ornithine, tert-butylglycine, 3-methoxyvaline, allothreonine, valine, threonine, leucine, isoleucine, lysine and methionine. More preferably, $A^2$ is selected from L-valine, L-leucine, L-lysine, L-methionine, L-threonine, L-isoleucine and L-tert-butylglycine. Most preferably, $A^2$ is L-valine or L-tert-butylglycine. As with the definition of $A^1$, one of skill in the art will understand that when $A^2$ is described as an amino acid or an amino acid fragment, what is meant is a residue of the amino acid that typically remains upon incorporation of the amino acid into a peptide or other similar linear array or polymer.

In Formula (I), the letter X represents a bond, a $(C_1–C_4)$ saturated or unsaturated alkyl linking group or a $(C_1–C_4)$ saturated or unsaturated heteroalkyl linking group. Preferably, X is $—OCH_2—$, $—CH_2CH_2—$, —CH=CH—, $—CH=C(CH_3)—$, $—C(CH_3)=CH—$, —C≡C—, $—NHCH_2—$, $—N(R)CH_2CH_2—$, —N=CH—, or —CH=N— in which R represents hydrogen or a lower alkyl group (e.g., methyl, ethyl, acetyl, propyl and the like). Most preferably, X represents a trans —CH=CH— linking group, a trans $—CH=C(CH_3)—$ linking group, or a —C≡C— linking group.

The symbols $D_a$, $D_b$ and $D_c$ each independently represent a divalent radical selected from =N— and $=C(R^9)—$, in which each $R^9$ is independently selected from hydrogen, halogen, cyano, nitro, $(C_1–C_6)$alkyl, $(C_1–C_6)$heteroalkyl, $(C_1–C_6)$alkoxy, $(C_1–C_6)$thioalkoxy, $—NR^{10}R^{11}$, $—C(O)OR^{10}$, $—C(O)NR^{10}R^{11}$, $—O—C(O)OR^{10}$, $—NR^{11}—C(O)OR^{10}$, $—NR^{10}—SO_2R^{12}$, $—NR^{10}—(CO)R^{11}$, $—SO_2NR^{10}R^{11}$, and $—OC(O)NR^{10}R^{11}$; in which $R^{10}$ and $R^{11}$ are each independently selected from hydrogen, $(C_1–C_8)$alkyl and $(C_1–C_8)$heteroalkyl. In an alternative embodiment, when $R^{10}$ and $R^{11}$ are attached to the same nitrogen atom they can be combined with each other to form a 5-, 6-, 7- or 8-membered ring containing from zero to three heteroatoms and each $R^{12}$ is independently selected from $(C_1–C_8)$alkyl, $(C_1–C_8)$heteroalkyl, aryl and heteroaryl.

The letters U and Z each independently represents a single bond, $—CH_2—$, —CH(OH)—, —C(O)—, $—CH_2O—$, $—CH_2CH_2—$, $—CH_2C(O)—$, —O—, —S—, $—S—CH_2—$, $—N(C(O)—(C_1–C_9)alkyl)-$, $—N(R^{13})—$ and $—N(R^{13})—CH_2—$, in which each $R^{13}$ is selected from hydrogen, $(C_1–C_8)$alkyl, aryl and $(C_1–C_8)$heteroalkyl;

In the above formula, $Y^1$ and $Y^2$ each independently represent $—CO_2H$ or $—CO_2R^{14}$, in which $R^{14}$ is selected from $(C_1–C_9)$alkyl, and $(C_1–C_9)$heteroalkyl. In an alternative embodiment, when $Y^1$ and $Y^2$ are each $—CO_2R^{14}$, each $R^{14}$ and the oxygen to which it is attached can join to form a 5-, 6-, 7- or 8-membered heterocyclic ring.

The above recitation provides general description of the embodiments and preferred embodiments for portions of the compounds of the present invention. Certain combinations of the components are particularly preferred. For example, in one particularly preferred embodiment, the compounds have the formula:

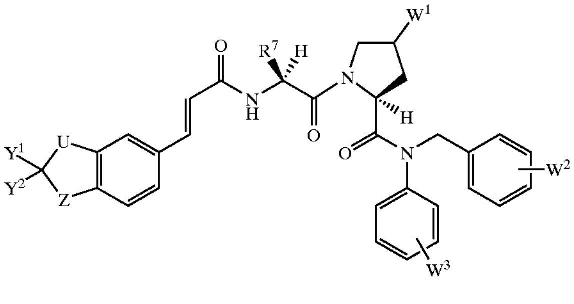

In the formula above, the letter $W^1$ represents —H, $—OR^{15}$ and $—NR^{15}R^{16}$, whereas the letters $W^2$ and $W^3$ each independently represent hydrogen, halogen, $—R^{17}$, $—CO_2R^{17}$, $—OR^{17}$, $—NR^{17}R^{18}$ and $—CONR^{17}R^{18}$, wherein $R^{15}$, $R^{16}$, $R^{17}$ and $R^{18}$ are each independently selected from hydrogen, aryl, $(C_1–C_8)$alkyl, $(C_1–C_8)$heteroalkyl, aryl$(C_1–C_8)$alkyl, aryl$(C_1–C_8)$heteroalkyl, alkylsulfonyl, arylsulfonyl and arylsulfinyl. In the formula above, the letters U and Z each independently represent $—CH_2—$, —CH(OH)—, —C(O)—, —O—, —S— and $—N(R^{13})—$.

In another group of particularly preferred embodiments, the compound has the formula:

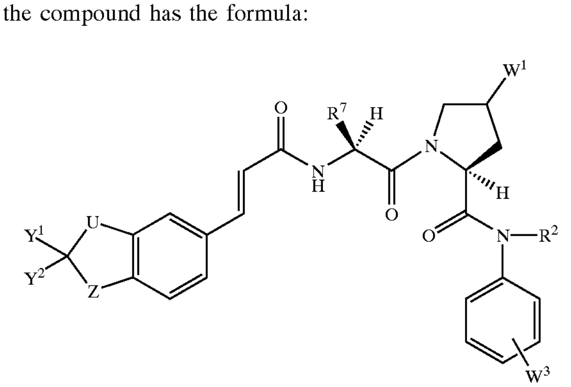

In the formula above, $R^2$ represents a substituted or an unsubstituted $(C_1–C_8)$alkyl. In the formula above, the symbol $W^1$ represents —H, $—OR^{15}$ and $—NR^{15}R^{16}$.

In the formula above, the symbol $W^2$ is selected from the group of hydrogen, halogen, $—R^{17}$, $—CO_2R^{17}$, $—OR^{17}$, $—NR^{17}R^{18}$ and $—CONR^{17}R^{18}$; wherein $R^{15}$, $R^{16}$, $R^{17}$ and $R^{18}$ are each members independently selected from the group consisting of hydrogen, aryl, $(C_1–C_8)$alkyl, $(C_1–C_8)$heteroalkyl, aryl$(C_1–C_8)$alkyl, aryl$(C_1–C_8)$heteroalkyl, alkylsulfonyl, arylsulfonyl and arylsulfinyl. In the formula above, the letters U and Z each members independently selected from the group consisting of $—CH_2—$, —CH(OH)—, —C(O)—, —O—, —S— and $—N(R^{13})—$.

In yet another group of particularly preferred embodiments, the compound has the formula:

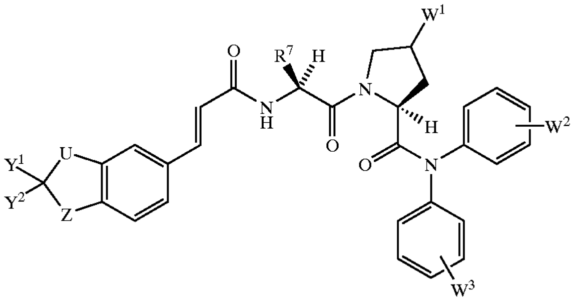

In the formula above, the symbol $W^1$ represents —H, —$OR^{15}$ and —$NR^{15}R^{16}$, whereas the symbols $W^2$ and $W^3$ each independently represent hydrogen, halogen, —$R^{17}$, —$CO_2R^{17}$, —$OR^{17}$, —$NR^{17}R^{18}$ and —$CONR^{17}R^{18}$; wherein $R^{15}$, $R^{16}$, $R^{17}$ and $R^{18}$ are each independently selected from hydrogen, aryl, $(C_1-C_8)$alkyl, $(C_1-C_8)$heteroalkyl, aryl$(C_1-C_8)$alkyl, aryl$(C_1-C_8)$heteroalkyl, alkylsulfonyl, arylsulfonyl and arylsulfinyl. The letters U and Z each independently represent —$CH_2$—, —CH(OH)—, —C(O)—, —O—, —S— and —$N(R^{13})$—

The compounds of the present invention are useful in therapeutic as well as prophylactic and diagnostic applications, and are also useful in drug discovery research. Accordingly, the present invention provides suitably modified derivatives of the above compound in such a manner that their interaction with a STAT6 molecule (or fragment thereof) can be easily detected by physical or chemical means. The present invention further provides compositions containing the above compounds and pharmaceutically acceptable excipients or diagnostically acceptable excipients. Still further, the invention provides methods of treating conditions or diseases, particularly those mediated by STAT6 signaling. Such conditions or diseases include allergic conditions (e.g., allergic rhinitis, asthma, atopic dermatitis, contact dermatitis, anaphylaxis, food or drug induced allergy, conjunctivitis, uveitis, hypersensitivity reactions, alveolitis and psoriasis), Churg-Strauss syndrome, delayed-type hypersensitivity, urticaria, angiodema, eczema, scleroderma, and systemic lupus erythematosus. In addition to treatments for existing conditions, the present invention also provides methods for prophylactic treatments to prevent the onset of the above-noted disorders in patients.

In still other embodiments, the invention provides methods of treating conditions such as those above, by administering to a subject in need of such treatment a therapeutic regimen comprising a compound provided herein, in combination with another agent such as, for example, loratadine, fluticasone propionate, beclametasono diproprionate, budesonide, salmeterol xinafoate, ipratropium bromide, fexofenadine hydrochloride, cetirizine dihydrochloride, triameinolone acetonide, cromolyn, salbutamol, montelukast sodium, ketotifen hydrogen fumarate, formoterol, zafirlukast, momefasone furoate, azelastine hydrochloride, epinastine, seratrodast, captropril, ramipril, zofenopril, colchioine, enalapril, lisinopril, trandolapril, gold sodium thiomalate, calcipotriene, cyclosporine, vinbiastine and dapsone.

In some cases, when combinations of therapeutic agents are used, the amount of each agent administered may be less than the amount required when the agent is used alone. In some embodiments, the agents are synergistic with the compounds provided herein and can be used in amount that are less than one-half of the normal efficacious dose. Additionally, when therapy is provided using a combination of agents, the administration of the agents can be simultaneous or sequential. In instances wherein administration is sequential, the agents can be administered in any order and the periods between administration of a first and second agent can be minutes, hours, days, weeks, or months.

Preparation of the Compounds

The compounds of the present invention can be prepared as generally set forth in FIGS. 1–4. One of skill in the art will appreciate that certain additional steps (e.g., protection and deprotection of certain labile substituents) may be necessary, but are easily accomplished by the skilled artisan.

FIG. 1 provides a general outline for the synthesis of compounds in which $A^1$ is an L-α-amino acid (alanine), $A^2$ is an L-α-amino acid (valine), and $R^1$ and $R^2$ are both aryl groups.

As shown in FIG. 1, treatment of Boc-protected L-alanine (i) with methyl 4-aminobenzoate (ii) in the presence of EDC provides amide iii. Treatment of iii with triphenylbismuth and copper(II) acetate provides diaryl amide iv. Removal of the Boc protecting group from iv and subsequent coupling with Boc-valine, followed by conversion of the methyl ester group to an amide (with ammonia) provides dipeptide v. Again, the removal of the Boc protecting group and acylation of the free amine with the acid vi, furnishes vii after ester hydrolysis (HCl, dioxane).

The general methodology outlined in FIG. 1 can be used with essentially any amino acids. For example, compounds of the present invention can be prepared by substituting Boc-alanine (i) with suitably protected forms of any of the following non-limiting examples: 2-aminoisobutyric acid, sarcosine, norvaline, homoserine, citrulline, norleucine, 2,3-diaminopropionic acid, methionine oxide, methionine dioxide, penicillamine, homoleucine, ornithine, $^3$H-dehydroproline, 2-methylproline, homoproline, 5-phenylproline, 4-chloroproline, proline, tyrosine, serine, and methionine. Similarly, Boc-valine can be substituted with suitably protected forms of, for example, norvaline, homoserine, cyclohexylalanine, norleucine, diaminopropionic acid, methionine oxide, homoleucine, ornithine, tert-butylglycine, 3-methoxyvaline, allothreonine, threonine, leucine, isoleucine, lysine and methionine. Similarly, the acid vi can be replaced in the synthesis scheme with a variety of other acids (see, for example, the acids depicted in FIG. 4).

Figure 2:
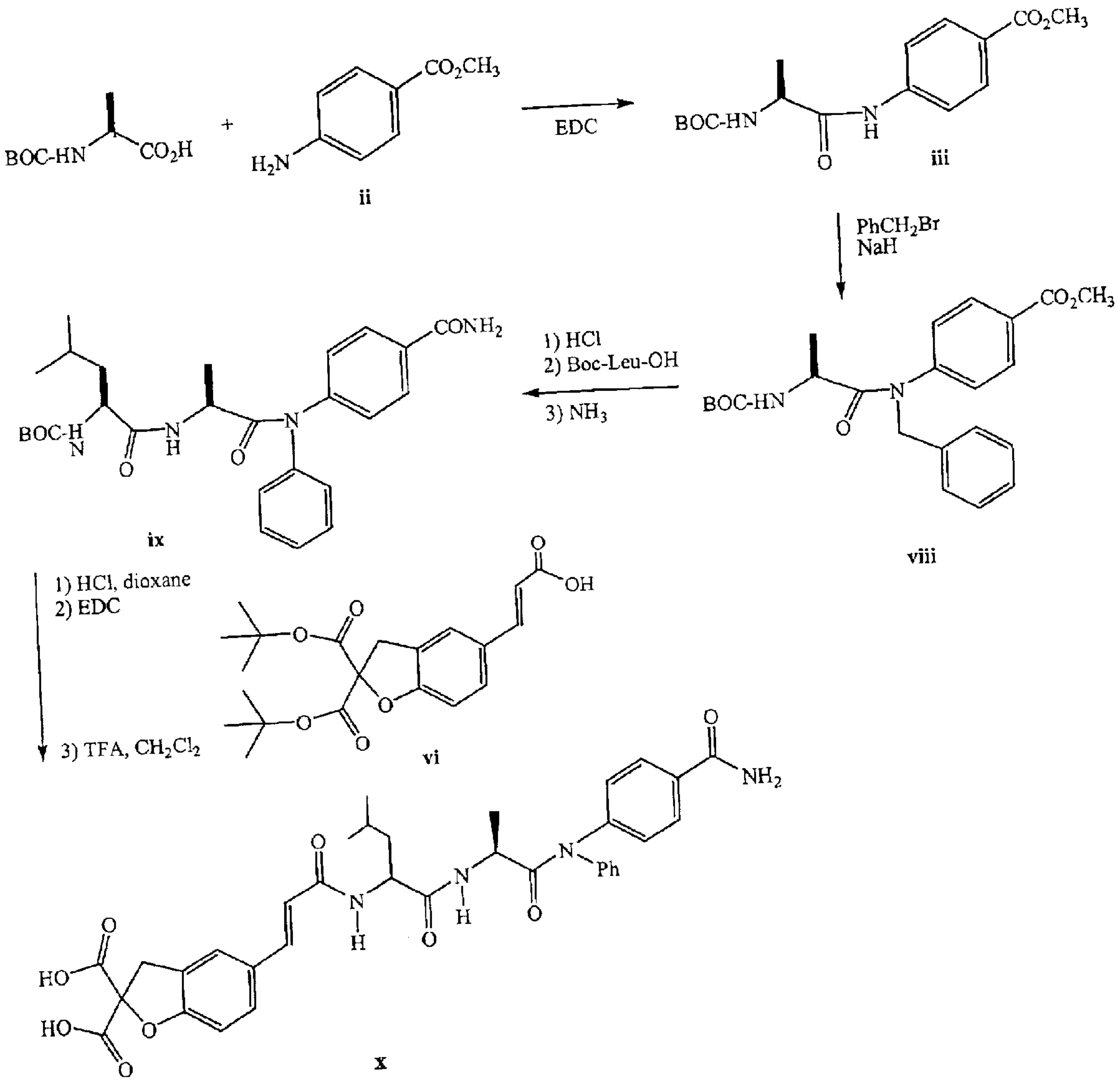
FIG. 2 illustrates a synthetic scheme to a particular embodiment of the present invention.

FIG. 2 illustrates a synthesis outline for the preparation of compounds in which $R^1$ is a substituted phenyl and $R^2$ is benzyl (or a substituted benzyl). In this scheme, synthesis begins as outlined in FIG. 1 to provide iii. Conversion of iii to amide viii can be accomplished by treating iii with sodium hydride and benzyl bromide. The remaining steps are essentially the same as those steps described in FIG. 1. Thus, removal of the Boc group in viii, followed by attachment of Boc-leucine and conversion of the methyl ester to an amide (with ammonia) results in formation of ix. Conversion of ix to x follows those steps, which were outlined for the conversion of v to vii.

Figure 3:
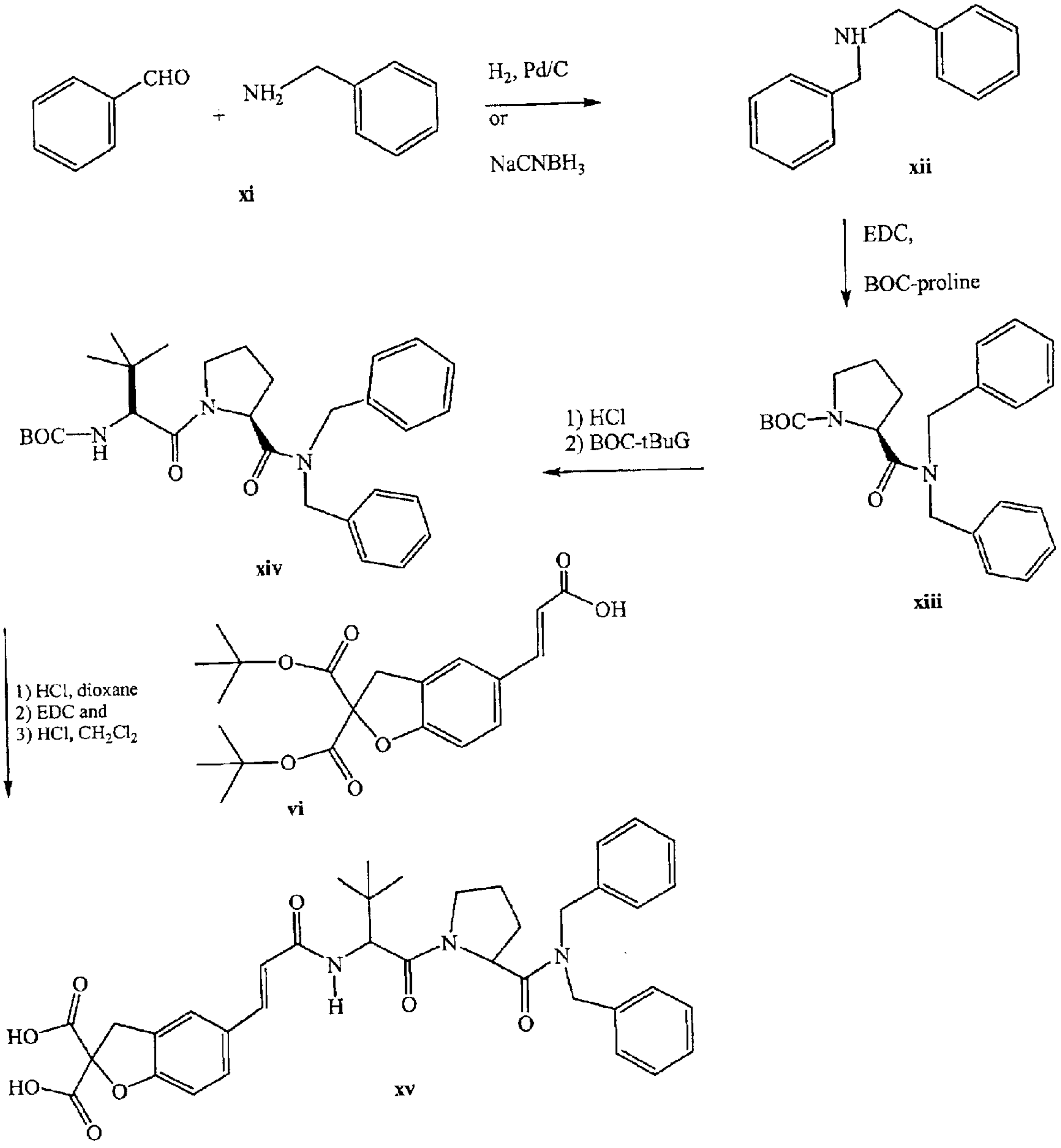
FIG. 3 illustrates a synthetic scheme to a particular embodiment of the present invention.

FIG. 3 provides a synthesis outline for compound in which $R^1$ and $R^2$ are each benzyl. One of skill in the art will understand that the method provided will be applicable to other arylalkylamines and substituted arylalkylamines. As illustrated in FIG. 3, condensation of benzaldehyde and benzylamine, and reduction of the Schiff base initially produced, yields dibenzylamine xii. Acylation of xii with Boc-proline provides xiii, which can be deprotected and acylated with Boc-t-butylglycine to provide xiv. Deprotection of xiv and acylation of the free amine xiv with the acid xiv provides the target compound xv after ester hydrolysis (HCl, $CH_2Cl_2$).

Substitution patterns on the benzene ring portions of $R^1$ and $R^2$ can be varied by starting the synthesis outlined in FIG. 3 with alternative substituted benzaldehydes and substituted benzylamines. Coupling the resultant dibenzylamine derivative with various amino acids (or alternatively, a dipeptide) and acylation of the N-terminous provides compound of the present invention.

Figure 4:
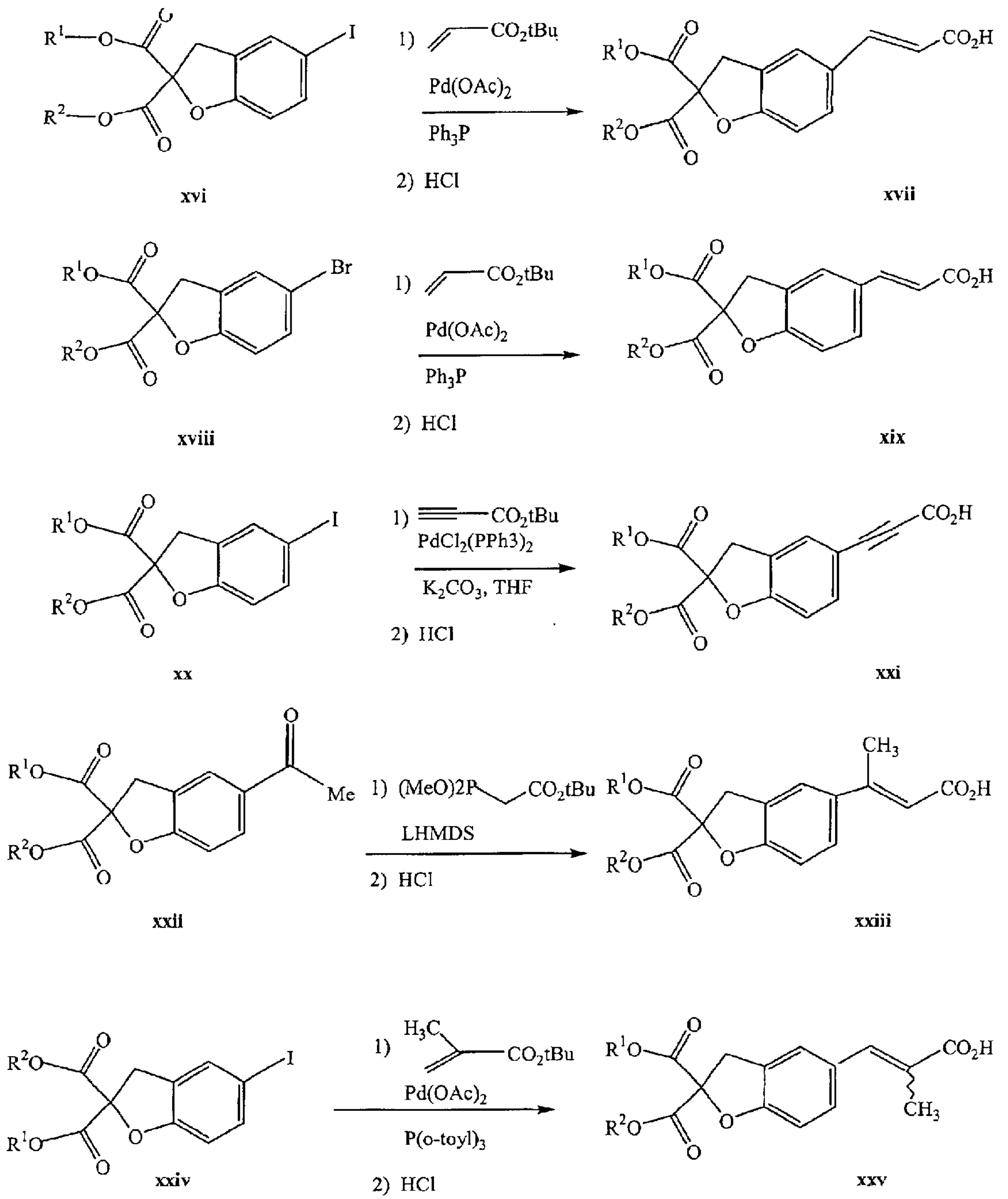
FIG. 4 illustrates a synthetic scheme to a particular embodiment of the present invention.

The starting materials used in the synthesis schemes above are generally commercially available or can be prepared using standard synthetic methodology. FIG. 4 provides reaction schemes for preparing carboxylic acids that effectively add

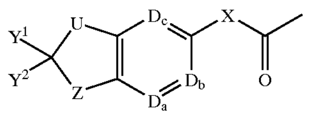

to the dipeptides v, ix and xiv (after removal of the Boc protecting group). After coupling of the groups to the dipeptides, the carboxylic acid and hydroxy protecting groups can be removed by standard basic conditions such as LiOH in a mixture of $MeOH/THF/H_2O$. For example, in FIG. 4, the reactants in column 1 (xvi, xviii, xx, xxii, and xxiv) can be converted to the acids (xvii, xix, xxi, xxiii, and xxv) upon treatment with t-butyl acrylate in the presence of palladium catalyst and triphenylphosphine, followed by treatment with HCl to remove the t-butyl ester.

Preparation of certain compounds of the invention can be accomplished using combinatorial methodology and/or solid phase synthesis. For example, an appropriately functionalized and protected diarylamine can be attached to a solid support. Removal of the protecting group and acylation of the free amine with an N-protected amino acid, or mixture of amino acids, will result in the corresponding amide. Subsequent removal of the protecting group and acylation of the free amine with a second N-protected amino acid, or mixture of amino acids, will result in the tethered dipeptide. Removal of the protecting group and acylation of the free amino group with a suitable carboxylic acid will provide the target compound(s) after cleavage from the solid support.

Preparation of certain compounds can be accomplished using combinatorial methodology or solid phase synthesis. Briefly, an appropriately functionalized and protected (with protecting group (PG)) diarylamine can be attached to a solid support. Removal of the protecting group and addition of an amino acid, or mixture of amino acids, results xx. Subsequent removal of the protecting group and addition of a second amino acid, or mixture of amino acids results in the tethered dipeptide xxi. Again, removal of the protecting group and acylation of the free amino group with an acid provides the target compounds xxii. Depending on the Nature of the protecting groups, a variety of automated synthesis formats can also be used for preparing the present compounds. A review of the methods (e.g., light-directed methods, pin-based methods, flow-channel methods and the like) can be found in U.S. Pat. Nos. 5,556,752 and 5,624,711.

Other useful methods for preparing the target compounds are those that obviate the need for certain protection and deprotection steps. For example, in FIG. 2, use of a symmetrical aryl dicarboxylic acid makes protection and deprotection of the distal (unreactive site) carboxylic acid unnecessary.

Analysis of the Compounds

The compounds of the present invention can be evaluated for STAT binding activity using methods such as those described in U.S. Pat. No. 6,207,391 (for STAT6 binding). Other assays for STAT binding can be found in, for example, U.S. Pat. Nos. 5,618,693, 5,639,858 and 5,756,700.

Formulation and Administration of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered topically, including transdermally. Accordingly, the present invention also provides pharmaceutical compositions comprising a pharmaceutically acceptable carrier or excipient and either a compound of formula I or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. Liquid forms are particularly preferred for topical applications to the eye. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from about 2 mg to about 2000 mg, preferably about 5 mg to about 150 mg according to the particular application and the potency of the active component. The composition can, if desired, also contain other compatible therapeutic agents (e.g., antiviral agents such as acyclovir, ganciclovir, foscarnet and cidofovir).

In therapeutic use as immunomodulators, the compounds utilized in the pharmaceutical method of the invention are administered at the initial dosage of about 0.05 mg/kg to about 20 mg/kg daily. A daily dose range of about 0.05 mg/kg to about 2 mg/kg is preferred, with a daily dose range of about 0.05 mg/kg to about 0.2 mg/kg being most preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

In certain embodiments, the present invention provides a method for modulating a STAT6-dependent condition in a host, comprising administering to the host a STAT6-modulating amount of a compound of Formula I. Various conditions include, but are not limited to, allergic rhinitis, asthma, atopic dermatitis, contact dermatitis, anaphylaxis, food or drug induced allergy, conjunctivitis, uveitis, hypersensitivity reactions, alveolitis, psoriasis, Churg-Strauss syndrome, delayed-type hypersensitivity, urticaria, angiodema, eczema, scleroderma, and systemic lupus erythematosus.

In certain aspects, the compound of Formula I is administered in combination with a second therapeutic agent. Suitable second therapeutic agents include, but are not limited to, loratadine, fluticasone propionate, beclametasone diproprionate, budesonide, salmeterol xinafoate, ipratropium bromide, fexofenadine hydrochloride, cetirizine dihydrochloride, triamcinolone acetonide, cromolyn, salbutamol, montelukast sodium, ketotifen hydrogen fumarate, formoterol, zafirlukast, momefasone furoate, azelastine hydrochloride, epinastine, seratrodast, captropril, rampril, zofenopril, colchicine, enalapril, lisinopril, trandolapril, gold sodium thiomalate, calcipotriene, cyclosporine, vinblastine dapsone and mixtures thereof. In certain aspects, the compound of Formula I and the second therapeutic agent are administered sequentially, or concurrently. In certain embodiments, the compound of Formula I and the second therapeutic agent are each administered at dosages of from 1/100 to 1/2 of their dosages when administered individually. In other embodiments, the compound of Formula I and the second therapeutic agent are each administered at dosages of from 1/10 to 1/4 of their dosages when administered individually.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). Electrospray ionization (ESI) mass spectrometry analysis was conducted on a Hewlett-Packard 1100 MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent.

Example 1

This example illustrates the synthesis of compound 1.

1

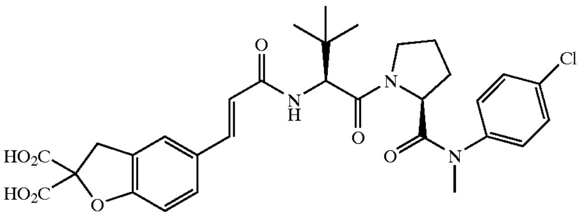

Preparation of Compound 1.1

1.1

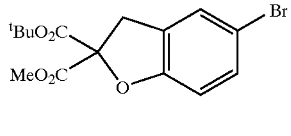

To a cooled (−78° C.) solution of tert-butyl methyl bromomalonate (10 g, 39.5 mmol) and 2-chloromethyl-4-bromophenol (8.75 g, 39.6 mmol) at −78° C. was added lithium bis(hexamethyldisilyl)amide (42 mL, 1.0 M in THF) dropwise. After 60 minutes at −78° C., the cooling bath was removed and the reaction mixture was allowed to warm to room temperature, diluted with saturated $NH_4Cl$ aqueous solution (200 mL). The phases were separated. The aqueous phase was extracted with $Et_2O$ (2×100 mL). The combined organic phases were dried over $MgSO_4$, and concentrated in vacuo. The residue was purified by silica gel flash chromatography (EtOAc/hexanes) to afford 12 g (85%) of white solid.

Preparation of Compound 1.2

1.2

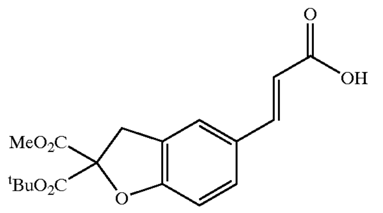

To a solution of 1.1 (3.0 g, 8.4 mmol) and acrylic acid (3 mL, 43.8 mmol) in $Et_3N$ (10 mL) and toluene (15 mL) was added $Pd(OAc)_2$ (0.56 g, 2.5 mmol) and tri-o-tolylphosphine (1.52 g, 5.0 mmol). The solution was heated to 100° C. and stirred for 4 hrs. The reaction was cooled to room temperature, diluted with EtOAc (200 mL) and 5% aqueous hydrochloric acid solution. The layers were separated. The organic layer was washed with brine (2×100 mL), dried over $MgSO_4$, filtered and concentrated in vacuo. The residue was purified by silica gel flash chromatography (EtOAc/hexanes) to yield 1.80 g (62%) of 1.2 as a white solid.

Preparation of Compound 1.3

1.3

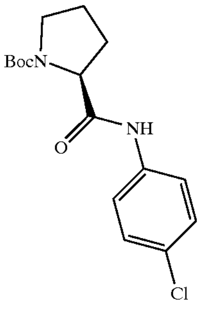

To a solution of 4-chloroaniline (8.8 g, 40.8 mmol) and Boc-L-proline (5.28 g, 37.3 mmol) were dissolved in DMF (100 mL) was added N-methylmorpholine (14 mL, 39.2 mmol) and O-benzotriazol-1-yl-N,N,N',N'-tetramethyluronium hexafluorophosphate (17.4 g, 45.8 mmol), 1-hydroxybenzotriazole hydrate (7.0 g, 39.2 mmol). After 16 hrs, the reaction was quenched with 10% aqueous citric acid solution. The phases were separated. The aqueous layer was extracted with EtOAc (3×100 mL). The combined organic layers were washed with saturated $NaHCO_3$ aqueous solution (2×100 mL), brine (100 mL), dried over $MgSO_4$, filtered and concentrated in vacuo. The crude residue was 13.3 g of 1.3, which was carried on to the next step without further purification.

Preparation of Compound 1.4

1.4

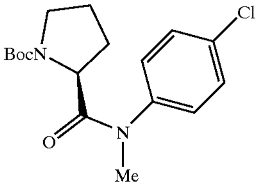

To a solution of ester 1.3 (13.3 g, 40.9 mmol) and iodomethane (3.5 g, 56.2 mmol) in $CH_2Cl_2$/DMF (1:1, 100 mL) at 0° C. was added NaH (60% dispersion in mineral oil, 2 g, 50 mmol) portionwise. The reaction mixture was stirred for 1 hr at 0° C., and then warmed to room temperature and stirred for 1.5 h. The reaction mixture was quenched with saturated $NH_4Cl$ aqueous solution. The layers were separated. The aqueous layer was extracted with EtOAc (2×100 mL). The combined organic layers were dried over $MgSO_4$, filtered and concentrated in vacuo. The residue was purified by silica gel chromatography (EtOAc/hexanes) to afford 11 g (81%, two steps) of 1.4 as a white foam.

Preparation of Compound 1.5

1.5

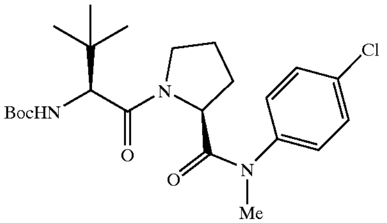

To a solution of 1.4 (7.3 g, 21.5 mmol) in EtOAc (150 mL) was added HCl (4 M in dioxane, 50 mL, 200 mmol). After 45 minutes at room temperature, the reaction was concentrated in vacuo. The residue was triturated with $CH_2Cl_2$ and the HCl salt produced was used without further purification.

The HCl salt was dissolved in DMF (100 mL). To this solution was added Boc-L-t-butyl glycine (6.8 g, 29.4 mmol) and N-methylmorpholine (10 mL, 90.6 mmol). Five minutes later O-benzotriazol-1-yl-N,N,N',N'-tetramethyluronium hexafluorophosphate (13 g, 34.2 mmol) and 1-hydroxybenzotriazole hydrate (5.4 g, 35.2 mmol) were added. The reaction was stirred for 8 hrs and then quenched with 10% aqueous citric acid solution. The aqueous layer was extracted with EtOAc (2×100 mL). The combined organic portions were washed with saturated $NaHCO_3$ solution, dried over $MgSO_4$, filtered and concentrated in vacuo. The residue was purified by silica gel chromatography (EtOAc/hexanes) to yield 7.9 g (81%) of 1.5 as a light yellow foam.

Preparation of Compound 1.6

1.6

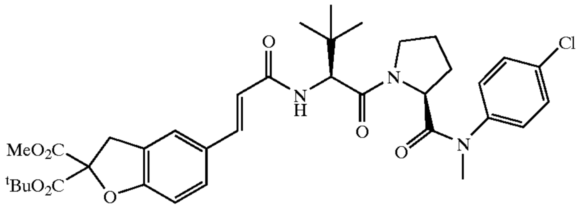

To a solution of 1.5 (204 mg, 0.59 mmol) in EtOAc (1 mL) was added HCl (4 M in dioxane, 2 mL). After 30 minutes, the reaction was concentrated in vacuo. The residue was triturated with $CH_2Cl_2$ and the HCl salt produced was used without further purification.

The HCl salt obtained above and 1.2 (227 mg, 0.5 mmol) were dissolved in DMF (2 mL). To this solution was added N-methylmorpholine (0.19, mL, 1.7 mmol). Five minutes later O-benzotriazol-1-yl-N,N,N',N'-tetramethyluronium hexafluorophosphate (0.24 mg, 0.63 mmol) and 1-hydroxybenzotriazole hydrate (0.1 mg, 0.6 mmol) were added. The reaction was stirred for 16 hrs and then quenched with 10% aqueous citric acid solution. The aqueous layer was extracted with EtOAc (2×50 mL). The combined organic portions were washed with saturated $NaHCO_3$ solution, dried over $MgSO_4$, filtered and concentrated in vacuo. The residue was purified by radial chromatography ($MeOH/CH_2Cl_2$) to yield 0.28 g (71%) of 1.6 as a light yellow foam.

Preparation of Compound 1

1

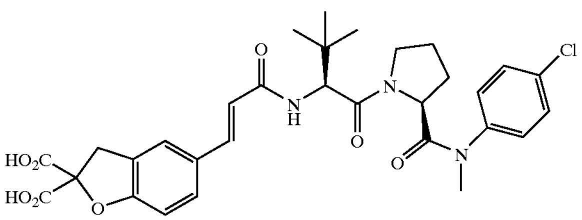

To ester 1.6 (236 mg, 0.35 mmol) in $THF/MeOH/H_2O$ (1:1:0.5 mL) was added LiOH (15 mg, 6 mmol). After 30 minutes, the reaction was quenched with 8 drops of acetic acid and the solution was concentrated in vacuo.

The crude mono-acid was dissolved in $CH_2Cl_2$(1 mL) and triflouroacetic acid (1 mL). The reaction mixture was stirred at room temperature for 1 hr. The solvent was removed in vacuo. The crude residue was purified by RP-HPLC to provide 112 mg (53%) of 1 as a white solid. $^1$N-NMR (400 MHz, $CD_3OD$): δ 7.35–7.43 (m, 7H), 6,86 (d, J=8.0 Hz, 1H), 6.60 (d, J=15.6 Hz, 1H), 4.66 (s, 1H), 4.29 (m, 1H), 3.96 (m, 1H), 3.75 (s, 2H), 3.75–3.71 (m, 2H), 3.21 (s, $^3$H), 2.01 (m, 1H), 1.80–1.88 (m, $^3$H), 1.09 (s, 9H); ); MS (ES−): 610.2 (M−H) 566.2.

Example 2

This example illustrates the synthesis of compound 2.

2

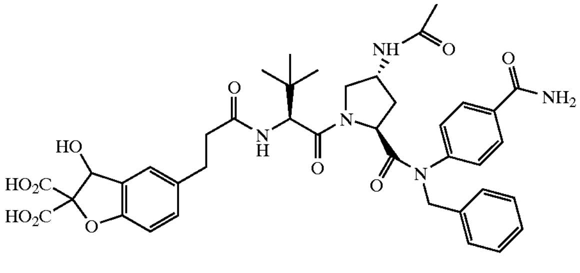

Preparation of Compound 2.1

2.1

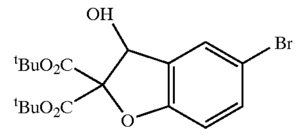

To a solution of di-tert-butyl bromomalonate (3 g, 10.2 mmol) and 5-bromosalicylaldehyde (2.25 g, 11.1 mmol) in 2-butanone (18 mL) was added potassium carbonate (2.1 g, 15 mmol). The reaction mixture was stirred at refluxing temperature for 1 hr. The reaction was cooled to room temperature, diluted with water and the phases were separated. The aqueous phase was extracted with $Et_2O$ (3×100 mL). The combined organic phases were washed with brine (100 mL), dried over $MgSO_4$, and concentrated in vacuo. The residue was purified by silica gel chromatography (EtOAc/hexanes) to afford 3.0 g (71%) of 2.1 as a clear oil.

Preparation of Compound 2.2

2.2

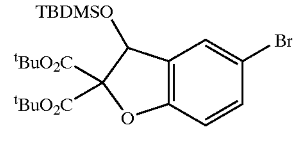

To a solution of tert-butyldimethylsilyl chloride (0.55 g, 3.6 mmol) and 2.1 (1 g, 2.4 mmol) in DMF (10 mL) was added imidazole (0.32 g, 4.8 mmol). The reaction mixture was stirred at room temperature for 48 hr. The reaction was diluted with $Et_2O$ (100 mL) and $NH_4Cl$ aqueous solution. The phases were separated and the organic phase was extracted with $Et_2O$ (3×100 mL). The combined organic phases were washed with brine (3×100 mL), dried over $MgSO_4$, filtered and concentrated in vacuo. The residue was purified by silica gel chromatography (EtOAc/hexanes) to afford 1.16 g (91%) of 2.2 as a light yellow oil.

Preparation of Compound 2.3

2.3

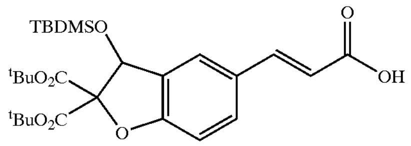

To a solution of 2.2 (0.5 g, 0.95 mmol) and acrylic acid (0.27 g, 3.3 mmol) in toluene (5 mL) was added $Pd(PPh_3)_4$ (0.33 g, 0.28 mmol) and $Et_3N$ (0.57 g, 5.7 mmol). The reaction was heated to 100° C. and stirred for 5 hrs. The reaction mixture was cooled to room temperature, diluted with EtOAc (150 mL) and 5% aqueous hydrochloric acid solution (50 mL). The layers were separated. The organic layer was washed with brine (2x50 mL), dried over $MgSO_4$, filtered through celite and concentrated in vacuo. The residue was purified by flash chromatography (EtOAc/hexanes) to yield 0.21 g (43%) of 2.3 as a light yellow oil.

Preparation of Compound 2.4

2.4

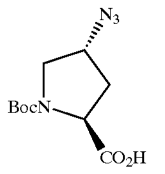

A solution of methyl Boc-cis-4-hydroxy-L-proline ester (1 g, 4.07 mmol) in 15 mL of $CH_2Cl_2$ was treated with $Et_3N$ (0.73 mL, 5.23 mmol), followed by methanesulfonyl chloride (0.37 mL, 4.76 mmol). The resulting solution was stirred for 30 min at 0° C. The cooling bath was removed and the reaction mixture was allowed to warm to room temperature and stirred for 3 h. The mixture was then diluted with saturated $NaHCO_3$ aqueous solution. The phases were separated. The aqueous phase was extracted with $CH_2Cl_2$ (2x50 mL). The combined organic layers were washed with brine (2x50 mL), dried over $MgSO_4$, filtered and concentrated in vacuo. The crude residue was carried on to the next step without further purification.

To the crude ester (0.72 g, 2.2 mmol) in DMF (4 mL) was added sodium azide (0.17 g, 2.6 mmol). The reaction was heated to 85° C. for 6 hr before it was cooled to room temperature. The reaction mixture was then diluted with water (50 mL) and EtOAc (100 mL). The layers was separated. The organic layer were washed with brine, dried over $MgSO_4$ and concentrated in vacuo. The crude product was carried to the next step without further purification.

To the crude azido methyl ester (0.58 g, 2.1 mmol) in THF/MeOH/$H_2O$ (2/2/1 mL) was added lithium hydroxide (0.15 g, 6.25 mmol). The resulting solution was stirred for 16 hr at room temperature. The reaction was diluted with 10% aqueous hydrochloric acid aqueous solution (10 mL) and EtOAc (50 mL). The phases were separated. The aqueous phase was extracted with EtOAc (3x50 mL). The combined organic phases were dried over $MgSO_4$, filtered and concentrated in vacuo. The crude product was carried to next step without further purification.

Preparation of Compound 2.5

2.5

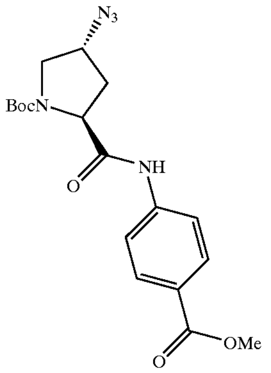

To a solution of compound 2.4 (0.58 g, 2.26 mmol) in DMF (5 mL) was added methyl 4-aminobenzoate (0.15 g, 6.25 mmol), N-methylmorpholine (0.29 mL, 2.6 mmol), O-benzotriazol-1-yl-N,N,N,'N'-tetramethyluronium hexafluorophosphate (0.95 g, 2.5 mmol), and 1-hydroxybenzotriazole hydrate (0.37 g, 2.41 mmol). The reaction mixture was stirred for 72 hrs, and then diluted with EtOAc (3x100 mL) and 10% citric acid aqueous solution (50 mL). The phases were separated. The organic phase was washed with saturated aqueous $NaHCO_3$ solution (50 mL) and brine (2x50 mL). The organic layer was dried over $MgSO_4$, filtered and concentrated in vacuo. The residue was purified by silica gel chromatography (EtOAc/hexanes) to afford 0.5 g (61%) of 2.5 as a light yellow foam.

Preparation of Compound 2.6

2.6

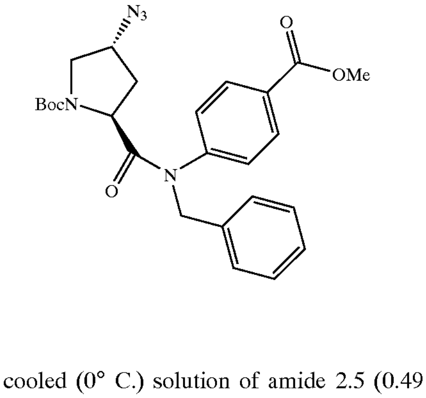

To a cooled (0° C.) solution of amide 2.5 (0.49 g, 1.41 mmol) and benzyl bromide (0.22 mL, 1.84 mmol) in DMF (2.5 mL) and $CH_2Cl_2$ (2.5 mL) was added NaH (60% dispersion in mineral oil, 67 mg, 1.7 mmol) portionwise. The solution was slowly warmed to room temperature and allowed to stir for 4 hrs. The reaction was quenched with saturated $NH_4Cl$ aqueous solution. The layers were separated. The aqueous layer was extracted with $CH_2Cl_2$ (3×50 mL). The combined organic layers were dried over $MgSO_4$, filtered and concentrated in vacuo. The resulting residue was purified by silica gel chromatography (EtOAc/hexanes) to provide 0.47 g (78%) of 2.6 as a light yellow foam.

Preparation of Compound 2.7

2.7

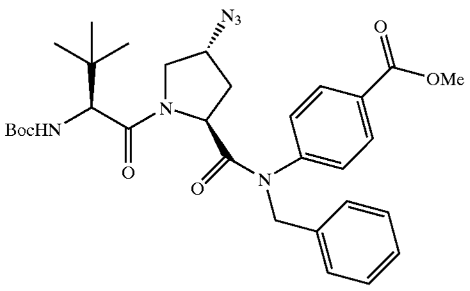

The tert-butyl carbamate 2.6 (0.47 g, 0.98 mmol) was stirred in HCl (4N in dioxane, 10 mL) and EtOAc (5 mL) for 30 minutes. The reaction mixture was concentrated in vacuo to afford the deprotected amine HCl salt that was used in the next reaction without further purification.

The crude material in DMF (3 mL) was added Boc-L-t-butylglycine (0.23 g, 0.98 mmol), 1-(3-dimethylaminopropyl)-3-ethylcarbodiimde hydrochloride (0.28 g, 1.46 mmol), 1-hydroxybenzotriazole hydrate (0.22 g, 1.46 mmol), and N-methylmorpholine (0.31 mL, 2.7 mmol). After stirring for 16 hr at room temperature, the reaction mixture was concentrated in vacuo. The residue was dissolved in EtOAc and washed with 10% aqueous citric acid, saturated $NaHCO_3$ aqueous solution and brine. The organic phase was dried over $MgSO_4$, filtered and concentrated in vacuo. The residue was purified by silica gel chromatography (EtOAc/hexanes) to yield 0.47 g (81%) of 2.7 as a white foam.

Preparation of Compound 2.8

2.8

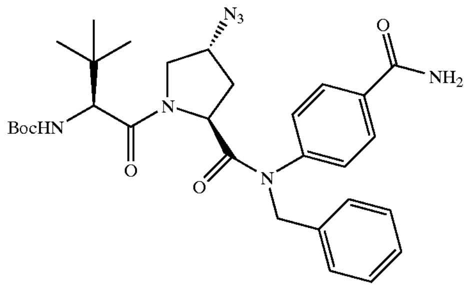

Ester 2.7 (0.47 g, 0.84 mmol) was dissolved in a saturated solution of ammonia in methanol (15 mL) and stirred in a sealed tube for 72 h at 75° C. The reaction was concentrated in vacuo and the residue purified by silica gel chromatography ($MeOH/CH_2Cl_2$) to afford 0.33 g (72%) of 2.8 as a light yellow foam.

Preparation of Compound 2.9

2.9

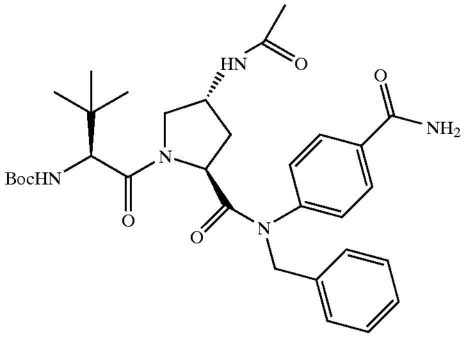

To a solution of azide 2.8 (0.33 g, 0.57 mmol) in methanol (10 mL) was added 10% Pd/C (33 mg). The flask was equipped with a balloon of $H_2$ and the reaction was stirred for 4 hrs at room temperature. The solution was filtered through celite, which was washed twice with MeOH, the filtrate was concentrated in vacuo, and the residue was used without further purification.

The residue was dissolved in $CH_2Cl_2$ (5 mL). To this solution was added acetic anhydride (59 μL, 0.63 mmol) and $Et_3N$ (0.1 mL, 1.0 mmol). After the reaction mixture was stirred for 16 hr, the reaction mixture was diluted with saturated $NH_4Cl$ aqueous solution and $CH_2C_{12}$. The layers were separated. The aqueous layer was extracted with $CH_2Cl_2$ (2×30 mL). The combined organic layers were dried over $MgSO_4$, filtered, and concentrated in vacuo. Purification by silica gel chromatography ($MeOH/CH_2Cl_2$) provided 0.28 g (84%) of 2.9 as a light yellow foam.

Preparation of Compound 2.10

2.10

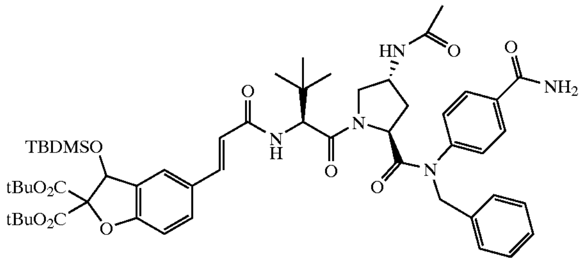

Amide 2.9 (0.12 g, 0.2 mmol) was stirred in HCl (4N in dioxane, 4 mL) for 30 minutes. The reaction mixture was concentrated in vacuo to afford the HCl salt of the corresponding deprotected amine, which was used in the next reaction without further purification.

The crude material from above was dissolved in DMF (6 mL). To this solution was added carboxylic acid 2.3 (0.1 g, 0.19 mmol), O-benzotriazol-1-yl-N,N,N',N'-tetramethyluronium hexafluorophosphate (86 mg, 0.22 mmol), 1-hydroxybenzotriazole hydrate (35 mg, 0.22 mmol), and N-methylmorpholine (62 μL, 0.57 mmol). After stirring overnight, the solvent was removed in vacuo. The residue was dissolved in EtOAc and the organic layer was washed with 10% aqueous citric acid and saturated aqueous $NaHCO_3$ solution. The organic layer was dried over $MgSO_4$, filtered, and concentrated in vacuo. Purification by radial chromatography ($MeOH/CH_2Cl_2$) provided 133 mg (71%) of 2.10 as a light yellow foam.

Preparation of Compound 2

2

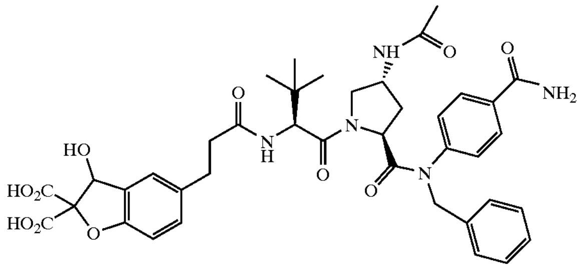

To a solution of 2.10 (64 mg, 0.06 mmol) in THF (2 mL) was added a solution of tetrabutylammonium chloride (70 $\mu$L, 1 M in THF). The reaction was stirred for 60 minutes at room temperature, and then it was diluted with saturated $NH_4Cl$ aqueous solution and extracted with EtOAc. The organic layer was dried over $MgSO_4$, filtered and concentrated in vacuo. The crude product was carried on to the next step without further purification.

To the crude di-tert-butyl ester in $CH_2Cl_2$(0.5 mL) was added triflouroacetic acid (0.3 mL) dropwise. The resulting solution was stirred for 1 hr at room temperature. The solvent was removed in vacuo. The residue was purification by RP-HPLC provided 18 mg (36%) of 2 as a white solid. $^1$N-NMR (400 MHz, $CD_3OD$): δ 7.83 (d, J=8.0 Hz, 2H), 7.60(s, 1H), 7.51 (d, J=4 Hz, 1H), 7.46 (d, J=15.6 Hz, 1H), 7.36 (d, J=8.0 Hz, 2H), 7.24 (s, 5H), 6.96(d, J=4 Hz, 1H), 6.71 (d, J=15.6 Hz, 1H), 5.82 (s, 1H), 5.18 (d, J=14.8 Hz, 1H), 4.82 (m, 1H), 4.63 (d, J=14.8 Hz, 1H), 4.55–4.49 (m, 5H), 3.94 (d, J=3.6 Hz), 2.18 (m, 1H), 1.95 (m, 1H), 1.85 (s, $^3$H), 1.14 (s, 9H); ). MS (ES+): 770.3 (M+H).

Example 3

3

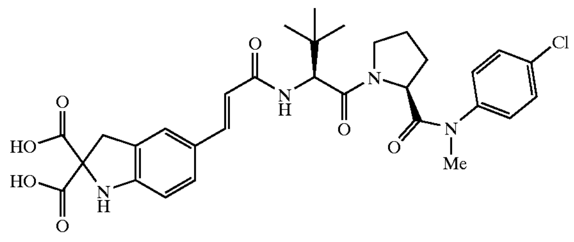

Preparation of Compound 3.1

3.1

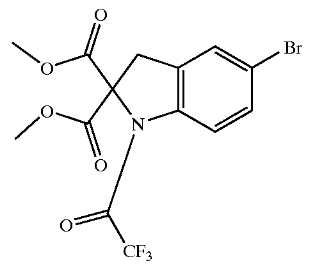

To a solution of 2-aminobenzyl alcohol (7.12 g, 58 mmol) in methylene chloride (200 mL) at −10° C., 2,4,4,6-tetrabromo-2,5-cyclohexadien-1-one (25 g, 61 mmol) was added in portions. During the addition, the temperature of the reaction mixture was maintained between −10° C. and 0° C. The reaction mixture was warmed up to room temperature and then extracted with 2 N sodium hydroxide solution (2×50 mL). The organic layer was washed with water and dried over $MgSO_4$, filtered and concentrated in vacuo to afford 2-amino-5-bromobenzylalcohol as a yellow solid which was used without further purification.

To a solution of 2-amino-5-bromobenzylalcohol (6.81 g, 33.7 mmol) and $NEt_3$ (6.63 mL, 47.2 mmol) in ethyl ether (120 mL) at 0° C., a solution of triflouroacetic anhydride (5.23 mL, 37 mmol) in ether (10 mL) was added dropwise. The mixture was then stirred at 0° C. for addition 1 hr. The reaction mixture was washed with 10% $H_2SO_4$ aqueous solution, dried over $MgSO_4$, filtered and concentrated in vacuo. The residue was then recrystallized by the addition with hexanes.

To a solution of the benzyl alcohol (2.98 g, 10 mmol) obtained in the previous paragraph in the mixture of ether and methylene chloride (10 mL:10 mL) was treated with $PBr_3$ (0.96 mL, 5.1 mmol). The reaction mixture was stirred at room temperature for 5 min, then heated under reflux for 30 min. The reaction mixture was quenched with a mixture of ether and ice water. The organic layers were separated and washed with water and brine. The organic layers were dried over $MgSO_4$, filtered and concentrated in vacuo. The residue was then recrystallized to afford an brownish solid by the addition with hexanes.

To a solution of benzyl bromide (1.05 g, 2.9 mmol) and dimethyl bromomalonate (0.87 g, 3.5 mmol) in THF at −78° C., a solution of LiHMDS (8.2 mL. 7 mmol, 1M solution in hexanes) was added dropwise. The reaction mixture was stirred at −78° C. for 1 hr, then quenched with saturated ammonium chloride solution, and extracted with ether (2×15 mL). The organic layers were then dried over $MgSO_4$, filtered and concentrated in vacuo. The residue was then purified by column chromatography on silica (10:1 hexanes-ethyl acetate) to a colorless oil (0.89 g, 71% yield over 4 steps). The overall steps to synthesize 3.1 are illustrated in Scheme 1 below.

Scheme 1

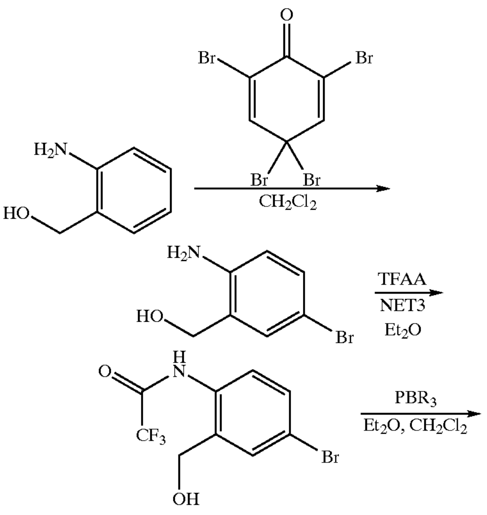

-continued

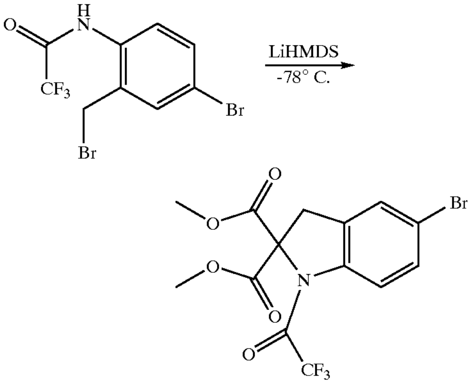

Preparation of Compound 3.2

3.2

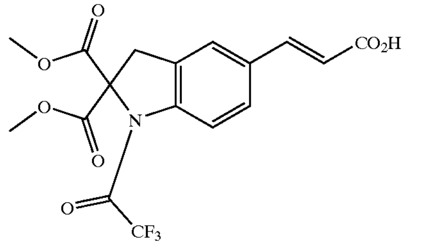

To a solution of the 3.1 (0.7 g, 1.7 mmol) and t-butyl acrylate (1.08 g, 8.5 mmol) in $Et_3N$ (10 mL) and toluene (5 mL) was added $Pd(OAc)_2$ (0.112 g, 0.5 mmol) and tri-o-tolylphosphine (0.304 g, 1 mmol). The solution was heated to reflux for 3 hrs. The reaction was cooled, filtered through celite, concentrated in vacuo, and purified by flash chromatography (EtOAc/hexanes) to afford the t-butyl ester of 3.2 as light yellow oil.

To a solution of t-butyl ester (0.49 g, 1.1 mmol) in $CH_2Cl_2$ (5 mL) at 0° C. was added TFA (5 mL) dropwise over 15 minutes. The resulting solution was warmed to room temperature and stirred for 1.5 h. The reaction was concentrated in vacuo and triturated with $CH_2Cl_2$ to afford 3.2 as a white solid (0.42 g, 61% over two steps).

Preparation of Compound 3

3

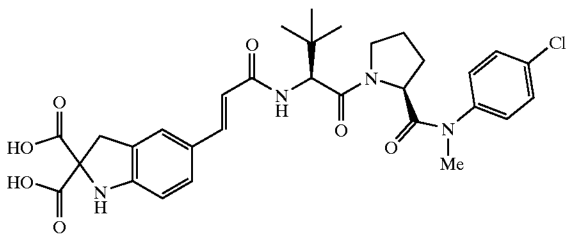

Using methods similar to those described in Example 1, compound 3 was prepared. Certain additional steps (deprotection of certain labile substituents) may be necessary, but are easily accomplished by the skilled artisan. The final product was purified by RP-HPLC to provide a white solid. $^1$H-NMR (400 MHz, $CD_3OD$): δ 7.22–7.94 (m, 7H), 6,86 (d, J=8.4 Hz, 1H), 6.34 (d, J=16.2 Hz, 1H), 4.64 (s, 1H), 4.31 (m, 1H), 3.48–3.80 (m, 4H), 3.23 (s, 3H), 1.72–2.05 (m, 4H), 1.12 (s, 9H). MS (ES−): 610.1 (M−H).

Example 4

4

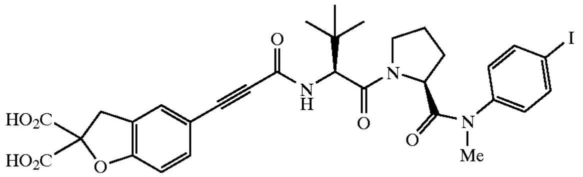

Preparation of Compound 4.1

4.1

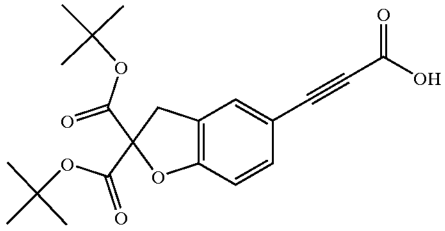

To a solution of 5-(2-carboxyvinyl)-3H-benzofuran-2,2-dicarboxylic acid di-tert-butyl ester (0.39 g, 1 mmol, prepared in a manner similar to intermediate 1.2) in methylene chloride (15 mL) at 0° C. was added dropwise bromine (0.16 g, 1 mmol) solution in 5 mL methylene chloride. After 1 hour, the solution was concentrated in vacuo to afford a light yellow solid, which was used without further purification.

To a solution of the crude dibromide (0.55 g, 1 mmol) in THF (20 mL) at 0° C. was added potassium t-butoxide solution (1 M solution in THF, 3.3 mL, 3.3 mmol). The resulting solution was stirred for 3 hours, diluted with saturated ammonium chloride solution (10 mL). The reaction mixture was extracted with EtOAc (3×15 mL), and the organic layer was dried over $MgSO_4$. The organic layer was then filtered, concentrated in vacuo, and purified by flash chromatography to yield 0.31 g (79% over two steps) of 4.1 as a white solid.

Preparation of Compound 4

4

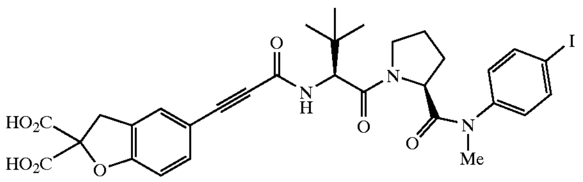

Using methods similar to those described in Example 1, the compound 4 was prepared from intermediate 4.1. The final product was purified by RP-HPLC to provide a white solid. $^1$N-NMR (400 MHz, $CD_3OD$): δ 7.23–7.85 (m, 6H), 6,87 (d, J=7 Hz, 1H), 4.86 (s, 1H), 4.25 (m, 1H), 3.68–3.80 (m, 4H), 3.23 (s, 3H), 1.62–2.05 (m, 4H), 1.12 (s, 9H). MS (ES−): 700.2 (M−H).

Example 5

5

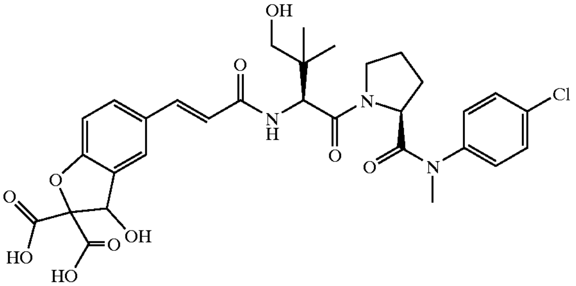

Preparation of Compound 5.1

5.1

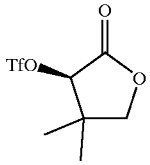

To a solution of (R)-(−)-pantolactone (5.0 g, 38.4 mmol) in 20 mL of dry dichloromethane was added pyridine (3.88 mL, 48.0 mmol). The resulting solution was cooled to −78° C. Triflic anhydride (11.9 g, 42.3 mmol) was added dropwise via a syringe over 10 min. The reaction mixture was stirred at −78° C. for 30 min and then 1 h at room temperature.

The reaction mixture was partitioned between 100 mL of diethyl ether and 100 mL of 10% aqueous $KHSO_4$. The organic layer was washed once with 50 mL of saturated $NaHCO_3$, followed by 50 mL of brine. It was dried over $Na_2SO_4$, and concentrated in vacuo to give 9.6 g (95%) of yellow oil as crude product 5.1, which was used in subsequent step without further purification.

$^1$H NMR (400 MHz, $CDCl_3$): 5.08 (s, 1H), 4.14 (d, 1H), 4.07 (d, 1H), 1.31 (s, 3H), 1.23 (s, 3H).

Preparation of Compound 5.2

5.2

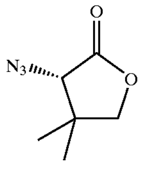

The crude product 5.1 (9.6 g, 36.6 mmol) obtained above was dissolved in 50 mL of DMF. To the resulting solution was added $NaN_3$ (2.75 g, 42.3 mmol). The mixture was stirred at room temperature for 3 h. The reaction mixture was poured into 200 mL of water. The aqueous mixture was extracted twice with 100 mL of diethyl ether. The combined organic extract was washed once with 70 mL of brine. The organic layer was dried over $Na_2SO_4$ and concentrated in vacuo to give 5.4 g (91%) of a clear oil 5.2 as crude product, which was used in subsequent step without further purification.

$^1$H NMR (400 MHz, $CDCl_3$): 4.14 (d, 1H), 4.03 (d, 1H), 3.99 (s, 1H), 1.25 (s, 3H), 1.12 (s, 3H).

MS (ESI, positive): 178.1.

Preparation of Compound 5.3

5.3

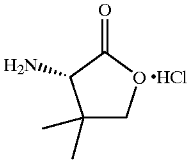

To a solution of the crude product 5.2 (5.4 g, 35 mmol) obtained above in 100 mL of MeOH, was add 3.5 mL of concentrated HCl (42 mmol), and 10% Pd on carbon (37 mg, 0.35 mmol). Hydrogen was introduced using a balloon. The mixture was stirred vigorously for 20 h at room temperature. The mixture was filtered through a pad of Celite. The filtrate was concentrated in vacuo to give 4.4 g (76%) of a white solid as product 5.3, which was used in subsequent step without further purification.

$^1$H NMR (400 MHz, DMSO-$d_6$): 7.93 (br s, 3H), 4.12 (s, 1H), 4.10 (d, 1H), 4.06 (s, 1H), 1.20 (s, 3H), 1.00 (s, 3H).

Preparation of Compound 5.4

5.4

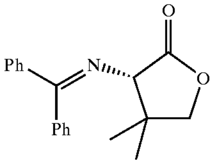

To a suspension of 5.3 (0.528 g, 3.19 mmol) in 5.5 mL of methylene chloride was added benzophenone imine (0.607 g, 3.35 mmol). After stirred at room temperature for 24 h, the mixture was filtered through a pad of Celite. The filtrate was concentrated in vacuo to give a colorless oil as crude product, which was purified by silica gel chromatography, eluted with 5% EtOAc in hexane, to give 0.832 g (89%) of 5.4 as a colorless oil.

$^1$H NMR (400 MHz, $CDCl_3$): 7.70 (dd, J=9.2, 1.2 Hz, 2H), 7.52–7.25 (m, 8H), 4.22 (d, J=8.8 Hz, 1H), 3.92 (s, 1H), 3.91 (d, J=8.8 Hz, 1H), 1.33 (s, 3H), 1.00 (s, 3H).

MS (ESI, positive): 294.2, 316.1.

Preparation of Compounds 5.6 and 5.7

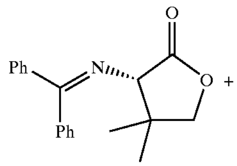

5.4

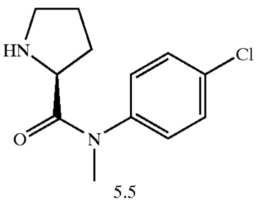

5.5

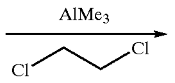

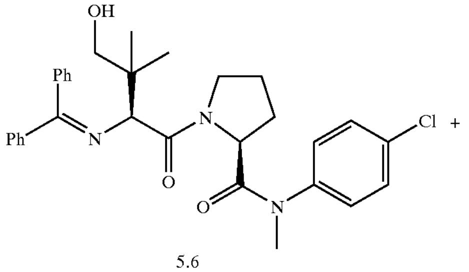

5.6

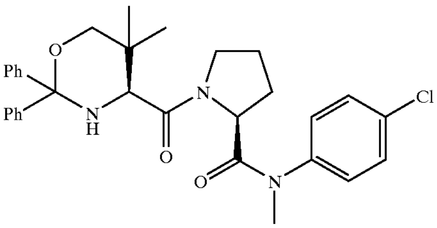

5.7

To a solution of 5.4 (246 mg, 0.84 mmol) and 5.5 (200 mg, 0.84 mmol, prepared from 1.5) in 2 mL of 1,2-dichloroethane was added $Me_3Al$ (0.524 mL, 1.05 mmol) via syringe. The mixture was heated to reflux for 2 h, and then cooled to room temperature. The reaction mixture was diluted with 20 mL of methylene chloride. Ground $Na_2SO_4.10OH_2O$ (1 g) was added. The mixture was stirred at room temperature for 16 h. The mixture was passed through a short column of silica gel, which was eluted with EtOAc. The eluent was concentrated in vacuo to give a yellow oil as crude product, which was purified by silica gel chromatography to give a mixture of structural isomers 5.6 and 5.7 as product. Combined yield of 5.6 and 5.7 was 196 mg (44%).

MS (ESI, positive): 532.3, 554.2.

Preparation of Compound 5.8

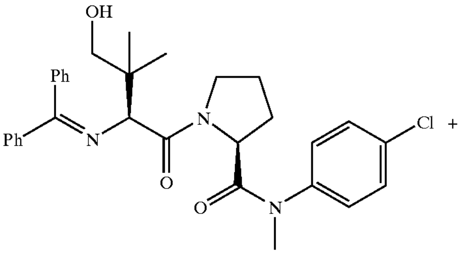

5.6

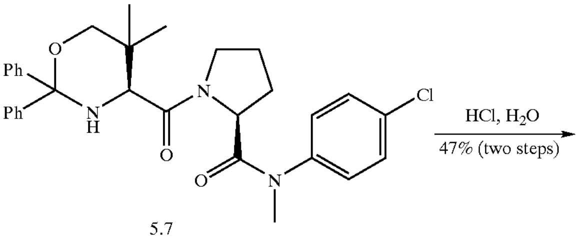

5.7

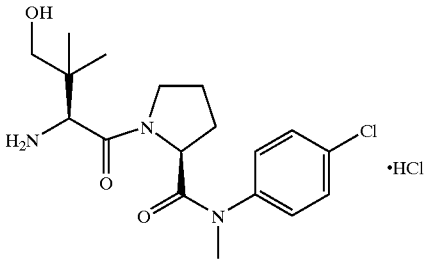

5.8

To a solution of the product mixture 5.6 and 5.7 obtained above (195 mg, 0.37 mmol) in 1.5 mL of MeOH and 1.5 mL of $H_2O$ was added 0.4 mL of a 3 M aqueous HCl solution. The reaction mixture was stirred at room temperature for 2 h. The mixture was diluted with 10 mL of $H_2O$ and washed twice with 3 mL of diethyl ether. The aqueous layer was first evaporated under reduced pressure to remove residual volatile organic solvent, and then lyophilized to give a white solid as product 5.8 (120 mg, 88%), which was used in subsequent reaction without further purification.

$^1H$ NMR (400 MHz, DMSO-$d_6$): 7.95 (m, 2H), 7.55 (m, 2H), 7.44 (m, 2H), 4.18–4.06 (m, 1H), 4.00 (m, 1H), 3.75–3.50 (m, 3H), 3.30 (d, 1H), 3.24 (d, 1H), 3.20–3.08 (m, 3H), 1.95–1.55 (m, 4H), 1.21–0.88 (m, 6H).

MS (ESI, positive): 368.1, 370.2.

Preparation of Compound 5.10

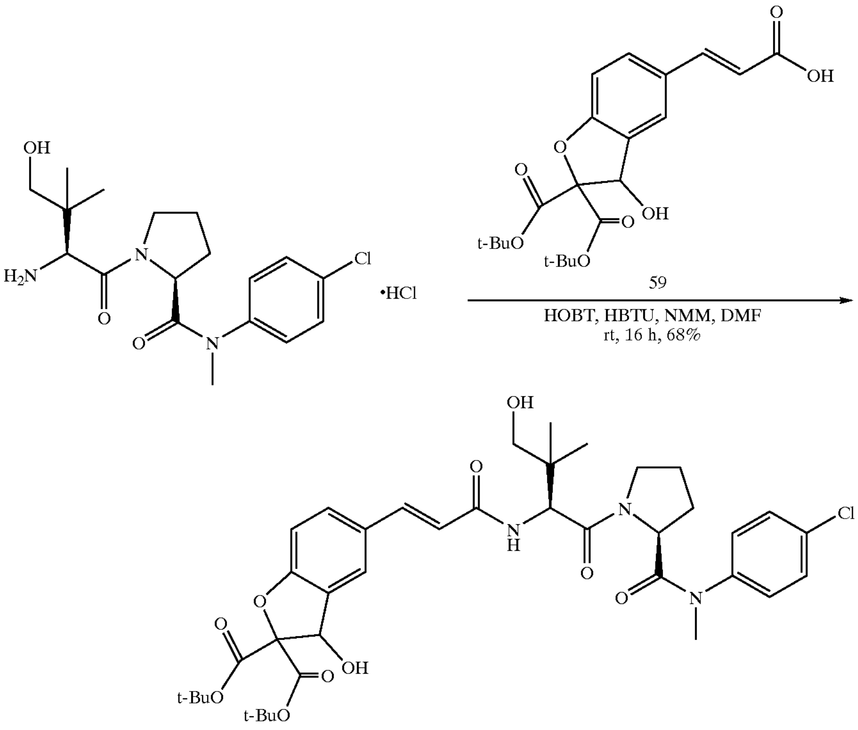

5.8 (51 mg, 0.13 mmol), 5.9 (51 mg, 0.13 mmol, prepared from 2.1 using a method similar to that used in the preparation of 2.3), HOBT (20 mg, 0.15 mmol), and HBTU (57 mg, 0.15 mmol) were dissolved in 1.0 mL of DMF. NMM (41 $\mu$L, 0.38 mmol) was added via syringe. The mixture was stirred at room temperature for 16 h. After dilution with 30 mL of EtOAc, the mixture was washed successively, twice with 15 mL of 5% $H_3PO_4$, once with 15 mL of saturated $NaHCO_3$, and 15 mL of brine. The organic layer was dried over $Na2SO_4$, and concentrated in vacuo to give a yellow foam as crude product, which was purified by preparative TLC, eluted with 10% MeOH in $CH_2Cl_2$, to give 65 mg (68%) of 5.10 as a white solid.

MS (ESI): 756.3, 758.3.

Preparation of Compound 7

7

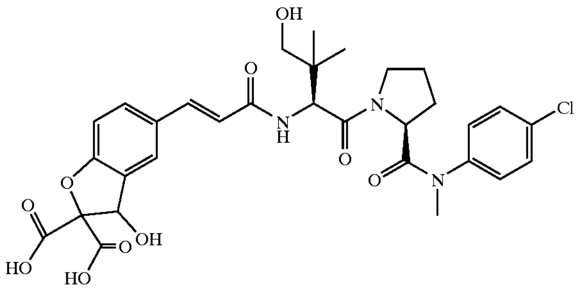

To a solution of 5.10 (65 mg, 86 $\mu$mol) obtained above in 0.25 mL of $CH_2Cl_2$, was added trifluoroacetic acid (0.20 mL, 2.58 mmol), and triethylsilane (69 $\mu$L, 0.43 mmol). The mixture was stirred at room temperature for 4 h, and evaporated in vacuo to give a brown residue, which was dissolved in 5 mL of 3:1 $H_2O$—MeCN, and purified by reverse phase HPLC to give 5.11 (26 mg, 47%) as a white solid.

$^1H$ NMR (400 MHz, DMSO-$d_6$): 8.45 (d, J=8.8 Hz, 1H), 7.97 (s, 1H), 7.73 (m, 2H), 7.68 (s, 1H), 7.60 (d, J=16 Hz, 1H), 7.54–7.35 (m, 2H), 6.95 (d, J=8.0 Hz, 1H), 6.80 (d, J=16 Hz, 1H), 5.67 (s, 1H), 4.89 (d, J=9.2 Hz, 1H), 4.12 (m, 2H), 4.02 (d, J=8.4 Hz, 1H), 3.75–3.15 (m, 6H), 3.10 (s, 3H), 1.95–1.65 (m, 4H), 1.10–0.85 (m, 6H).

Example 6

Using methods similar to those described in Examples 1–3, the compounds provided in Table 1 were prepared and evaluated as inhibitors of STAT6. Using the assay described in co-pending application U.S. Ser. No. 09/053,003, filed Mar. 31, 1998, the $IC_{50}$ values of these compounds were determined to be below 50 $\mu$M.

TABLE 1

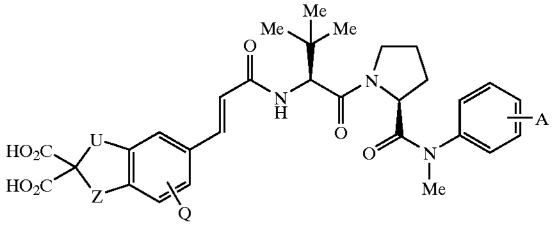

| No. | —U | —Z | —A | —Q |
|---|---|---|---|---|
| 6a | —CH(OH)— | —O— | — | — |
| 6b | —CH(OH)— | —O— | 4-Me | — |
| 6c | —CH(OH)— | —O— | 4-$CF_3$ | — |

TABLE 1-continued

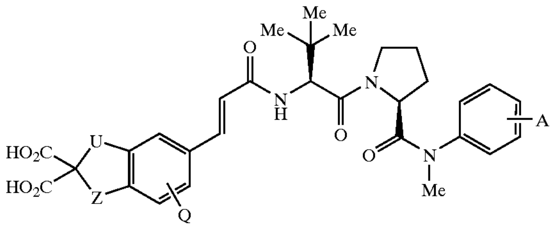

| No. | —U | —Z | —A | —Q |
|---|---|---|---|---|
| 6d | —CH(OH)— | —O— | 4-I | — |
| 6e | —CH(OH)— | —O— | 3-Cl | — |
| 6f | —CH(OH)— | —O— | 3,4-Cl | — |
| 6g | —CH(OH)— | —O— | 3-Cl | — |
| 6h | —CH(OH)— | —O— | 4-OMe | — |
| 6i | —CH(OH)— | —O— | 3-Me | — |
| 6j | —CH(OH)— | —O— | 3-$CONH_2$ | — |
| 6k | —$CH_2$— | —NH— | 4-I | — |
| 6l | —$CH_2$— | —O— | 4-CN | — |
| 6m | —$CH_2$— | —O— | 4-Ph | — |
| 6n | —$CH_2$— | —O— | 4-tBu | — |
| 6o | —$CH_2$— | —O— | 4-I | 4-Cl |
| 6p | —$CH_2$— | —O— | 4-I | 6-Cl |
| 6q | —$CH_2$— | —O— | 4-I | 4-Me |
| 6r | —$CH_2$— | —O— | 4-I | 6-Me |

Some of the following compounds exist in an equilibrium between two rotamers at room temperature. Only the NMR data of the major rotamer is reported.

Example 6a

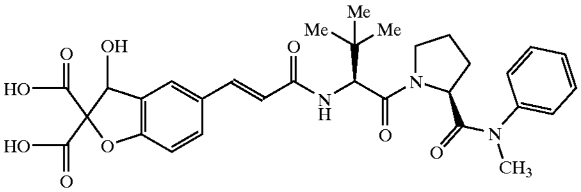

$^{1}$H NMR ($CD_3OD$) δ 7.5 (m, 8H), 6.95 (d, J=8.4 Hz, 1H), 6.70 (d, J=16.0 Hz, 1H), 5.83 (s, 1H), 4.64 (s, 1H), 4.30 (t, J=7.7 Hz, 1H), 3.97 (m, 1H), 3.70 (m, 1H), 3.21 (s, 3H), 2.20–1.75 (m, 4H), 1.16 (s, 9H). MS (ES, M−H+) 592.

Example 6b

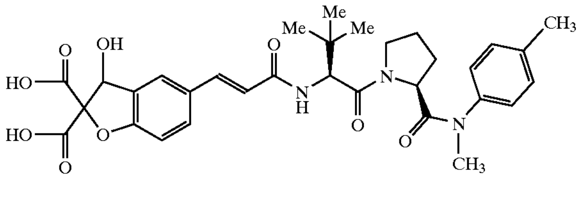

$^{1}$H NMR ($CD_3OD$) δ 7.5 (m, 7H), 6.95 (d, J=8.4 Hz, 1H), 6.70 (d, J=16.0 Hz, 1H), 5.83 (s, 1H), 4.64 (s, 1H), 4.30 (t, J=7.7 Hz, 1H), 3.97 (m, 1H), 3.70 (m, 1H), 3.21 (s, 3H), 2.32 (s, 3H), 2.20–1.75 (m, 4H), 1.16 (s, 9H). MS (ES, M−H+) 606.

Example 6c

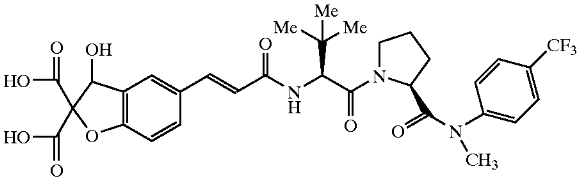

$^{1}$H NMR ($CD_3OD$) δ 7.5 (m, 7H), 6.95 (d, J=8.4 Hz, 1H), 6.70 (d, J=16.0 Hz, 1H), 5.83 (s, 1H), 4.64 (s, 1H), 4.30 (t, J=7.7 Hz, 1H), 3.97 (m, 1H), 3.70 (m, 1H), 3.24 (s, 3H), 2.20–1.75 (m, 4H), 1.16 (s, 9H). MS (ES, M−H+) 660.

Example 6d

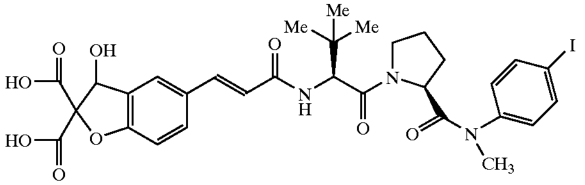

$^{1}$N-NMR ($CD_3OD$): δ 7.23–7.80 (m, 7H), 6.97 (m, 1H), 6.69 (d, J=15.84 Hz, 1H), 5.83 (s, 1H), 4.64 (s, 1H), 3.71–4.31 (m, 3H), 3.22 (s, 3H), 1.81–2.05 (m, 4H), 1.12(s, 9H). MS (ES−): 719 (M−H, 100).

Example 6e

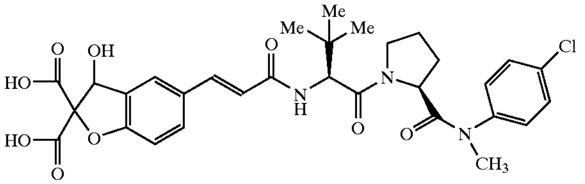

$^{1}$H NMR ($CD_3OD$) δ 7.5 (m, 7H), 6.95 (d, J=8.4 Hz, 1H), 6.70 (d, J=16.0 Hz, 1H), 5.83 (s, 1H), 4.64 (s, 1H), 4.30 (t, J=7.7 Hz, 1H), 3.97 (m, 1H), 3.70 (m, 1H), 3.22 (s, 3H), 2.20–1.75 (m, 4H), 1.16 (s, 9H). MS (ES, M−H+) 627.

Example 6f

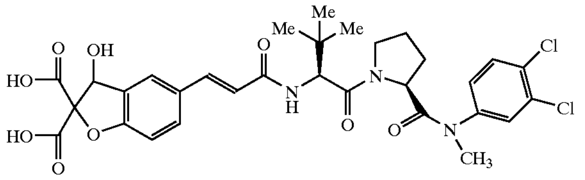

$^{1}$H NMR ($CD_3OD$) δ 7.5 (m, 6H), 6.95 (d, J=8.4 Hz, 1H), 6.70 (d, J=16.0 Hz, 1H), 5.83 (s, 1H), 4.64 (s, 1H), 4.30 (t, J=7.7 Hz, 1H), 3.97 (m, 1H), 3.70 (m, 1H), 3.23 (s, 3H), 2.20–1.75 (m, 4H), 1.16 (s, 9H). MS (ES, M−H+) 661.

Example 6g

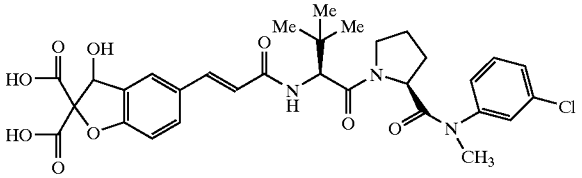

$^1H$ NMR ($CD_3OD$) δ 7.5 (m, 7H), 6.95 (d, J=8.4 Hz, 1H), 6.70 (d, J=16.0 Hz, 1H), 5.83 (s, 1H), 4.64 (s, 1H), 4.30 (t, J=7.7 Hz, 1H), 3.97 (m, 1H), 3.70 (m, 1H), 3.23 (s, 3H), 2.20–1.75 (m, 4H), 1.16 (s, 9H). MS (ES, M−H+) 627.

Example 6h

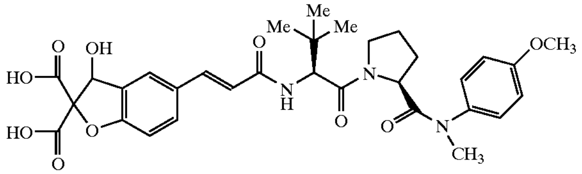

$^1H$ NMR ($CD_3OD$) δ 7.65–6.90 (m, 8H), 6.70 (d, J=16.0 Hz, 1H), 5.83 (s, 1H), 4.64 (s, 1H), 4.30 (t, J=7.7 Hz, 1H), 3.97 (m, 1H), 3.81 (s, 3H), 3.70 (m, 1H), 3.20 (s, 3H), 2.20–1.75 (m, 4H), 1.16 (s, 9H). MS (ES, M−H+) 622.

Example 6i

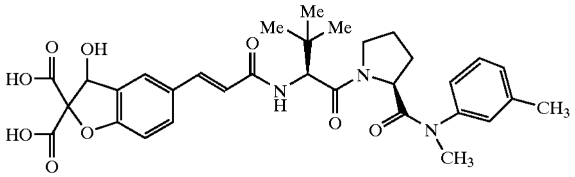

$^1H$ NMR ($CD_3OD$) δ 7.65–6.90 (m, 8H), 6.70 (d, J=16.0 Hz, 1H), 5.83 (s, 1H), 4.64 (s, 1H), 4.30 (t, J=7.7 Hz, 1H), 3.97 (m, 1H), 3.70 (m, 1H), 3.22 (s, 3H), 2.36 (s, 3H), 2.20–1.75 (m, 4H), 1.16 (s, 9H). MS (ES, M−H+) 606.

Example 6j

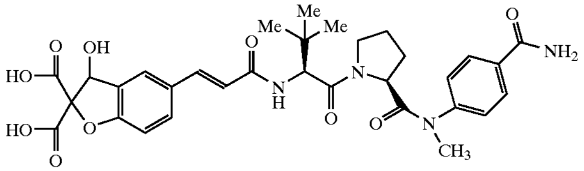

$^1H$ NMR ($CD_3OD$) δ 7.95 (d, J=8.5 Hz, 2H), 7.5 (m, 5H), 6.95 (d, J=8.4 Hz, 1H), 6.70 (d, J=16.0 Hz, 1H), 5.83 (s, 1H), 4.64 (s, 1H), 4.30 (t, J=7.7 Hz, 1H), 3.97 (m, 1H), 3.70 (m, 1H), 3.22 (s, 3H), 2.20–1.75 (m, 4H), 1.16 (s, 9H). MS (ES, M−H+) 635.

Example 6k

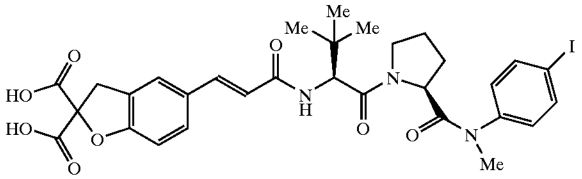

$^1N$-NMR ($CD_3OD$): δ 7.22–7.93 (m, 7H), 6.88 (d, J=8.4 Hz, 1H), 6.64(d, J=15.48 Hz, 1H), 4.64(m, 1H), 4.31(m, 1H), 3.96(m, 1H), 3.76(s, 2H), 3.71(m, 1H), 3.22 (s, 3H), 1.81–2.05(m, 4H), 1.11(s, 9H). MS (ES−): 702 (M−H, 100).

Example 6l

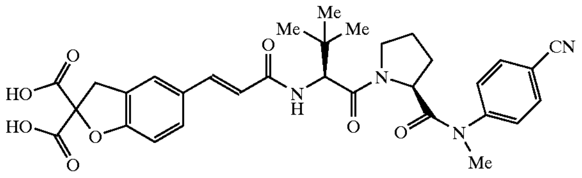

$^1N$-NMR ($CD_3OD$): δ 7.37–7.95 (m, 7H), 6.91 (m, 1H), 6.65(d, J=15.68 Hz, 1H), 3.99(m, 1H), 4.33(m, 1H), 3.73(m, 1H), 3.29(s, 3H), 1.84–2.09 (m, 4H) 1.11(s, 9H). ). MS (ES−): 601 (M−H, 55).

Example 6m

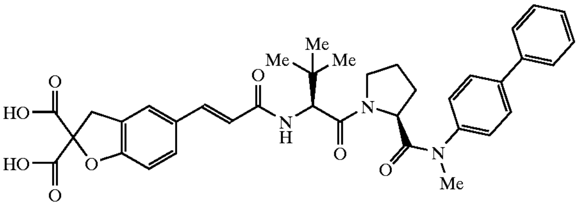

$^1H$-NMR ($CD_3OD$): δ 7.33–7.81 (m, 12), 6.88 (m, 1H), 6.63 (d, J=15.76 Hz, 1H), 4.66(d, J=2.56 Hz, 1H), 4.42 (m, 1H), 3.74 (m, 4H), 3.27 (s, 3H), 1.8–2.2 (m, 4H), 1.14(s, 9H). MS (ES−): 652 (M−H, 35).

Example 7

Using methods similar to those described in Examples 1–3, the compounds provided in Table 2 were prepared and evaluated as inhibitors of STAT6. All the compounds listed were found to possess $IC_{50}$ values <50 mM.

TABLE 2

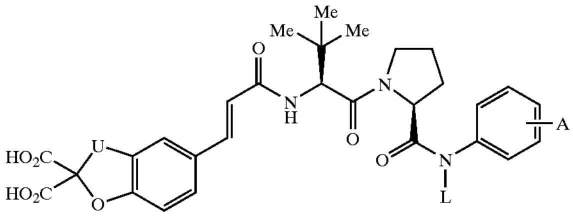

| No. | —L | —U | —A |
|---|---|---|---|
| 7a | 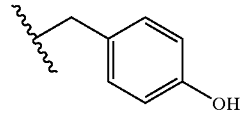 | —CH(OH)— | 4-Cl |
| 7b | 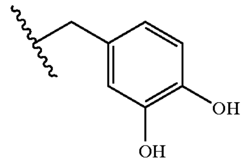 | —CH(OH)— | 4-Cl |
| 7c | 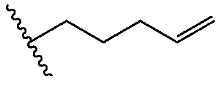 | —CH(OH)— | 4-Cl |
| 7d | 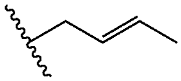 | —CH(OH)— | 4-Cl |
| 7e | 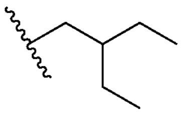 | —CH(OH)— | 4-Cl |
| 7f | 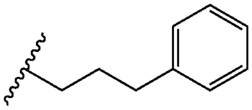 | —CH(OH)— | 4-Cl |
| 7g | 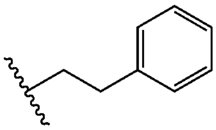 | —CH(OH)— | 4-Cl |
| 7h | 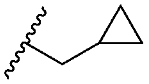 | —CH(OH)— | 4-Cl |
| 7i | 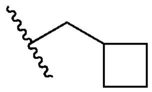 | —CH(OH)— | 4-Cl |
| 7j | 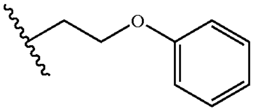 | —CH(OH)— | 4-Cl |

Example 8

The compounds provided in Table 3 were prepared using methods similar to those described in Examples 1–3. The compounds were evaluated using an STAT6 DNA binding assay (EMSA) using BJAB cells. All the compounds listed were found to possess $IC_{50}$ values <100 mM.

TABLE 3

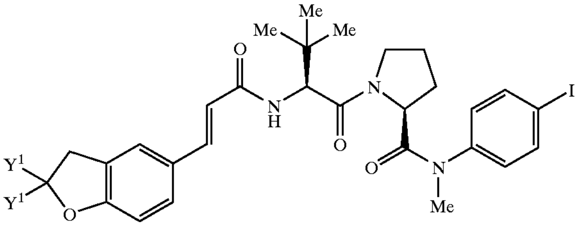

| No. | —$Y^1$ | —$Y^2$ |
|---|---|---|
| 8a | —$CO_2Me$ | —$CO_2Me$ |
| 8b | —$CO_2Et$ | —$CO_2Et$ |
| 8c | —$CO_2CH_2CH_2OMe$ | —$CO_2CH_2CH_2OMe$ |
| 8d | —$CO_2(CH_2CH_2O)_2Me$ | —$CO_2(CH_2CH_2O)_2Me$ |

Example 8a

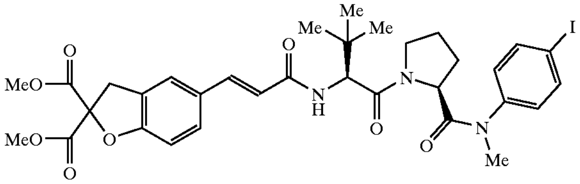

8a was synthesized in a manner similar to 1.6 by starting with the dimethyl ester analog of 1.1.

$^{1}$N-NMR ($CD_3OD$): δ 7.23–7.80 (m, 7), 6.87(m, 1H), 6.64 (d, J=15.72 Hz, 1H), 4.64 (s, 1H), 4.31(m, 1H), 3.69–3.9(m, 10H), 3.22(s, 3H), 1.81–2.05 (m, 4H), 1.12(s, 9H). MS (ES+): 732 (M+H, 80).

Example 8b

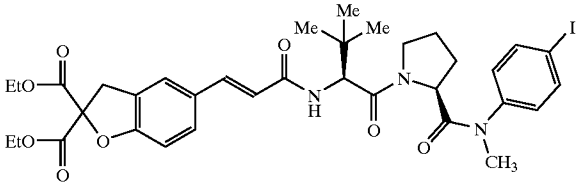

8b was synthesized in a manner similar to 1.6 by starting with the diethyl ester analog of 1.1.

$^{1}$H NMR ($CD_3OD$) δ 7.78 (d, J=8.4 Hz, 2H), 7.40 (m, 3H), 7.23 (d, J=8.4 Hz, 2H), 6.87 (d, J=8.4 Hz, 1H), 6.65 (d, J=16.0 Hz, 1H), 4.64 (s, 1H), 4.28 (m, 5H), 3.97 (m, 1H), 3.77 (s, 2H), 3.70 (m, 1H), 3.22 (s, 3H), 2.20–1.75 (m, 4H), 1.28 (t, J=7.1 Hz, 6H), 1.19 (s, 9H). MS (ES, M+H+) 760.

Example 8c

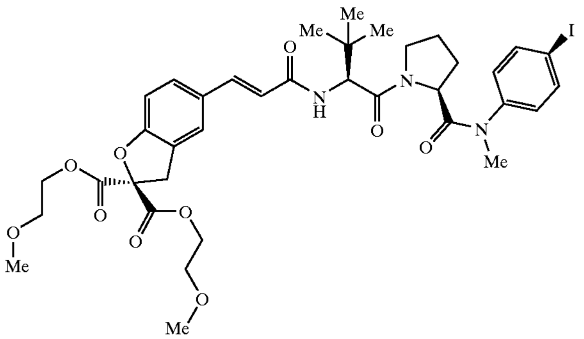

To a solution of 8a (160 mg, 0.22 mmol) in 2-methoxyethanol (1 mL), was added titanium isopropoxide (6.5 $\mu$L, 22 $\mu$mol) via syringe. The mixture was heated in a 100° C. oil bath for 45 min, and cooled to room temperature. The reaction mixture was then evaporated in vacuo to remove most of the solvent. The residue was purified by preparative TLC to give 145 mg (92%) of 8c as a white solid.

$^1$H NMR (400 MHz, DMSO-d$_6$): 8.09–7.75 (m, 3H), 7.70–7.35 (m, 2H), 7.32 (d, J=15.6 Hz, 1H), 7.23 (m, 2H), 7.00 (m, 1H), 6.91–6.75 (m, 1H), 4.61 (d, J=9.2 Hz, 1H), 4.33 (m, 4H), 4.17 (m, 1H), 3.79 (s, 2H), 3.74 (m, 1H), 3.62 (m, 1H), 3.55 (t, J=4.6 Hz, 4H), 3.25 (s, 6H), 3.12 (m, 3H), 2.10–1.75 (m, 4H), 1.05–0.70 (m, 9H). MS (ESI, positive): 820.1, 842.2.

Example 8d

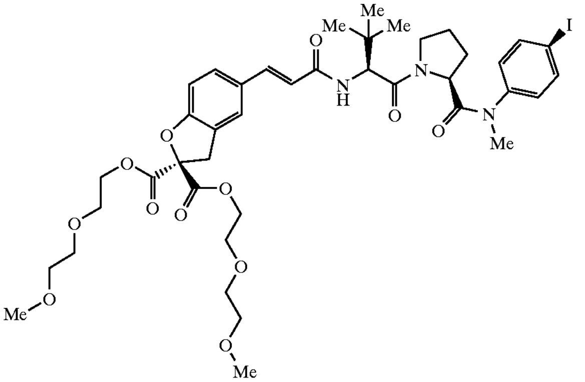

8d was synthesized in a similar manner as described for 8c.

$^1$H NMR (400 MHz, DMSO-d$_6$): 8.09–7.75 (m, 3H), 7.70–7.35 (m, 2H), 7.32 (d, J=15.6 Hz, 1H), 7.23 (m, 2H), 7.00 (m, 1H), 6.91–6.75 (m, 1H), 4.61 (d, J=9.2 Hz, 1H), 4.33 (m, 4H), 4.17 (m, 1H), 3.79 (s, 2H), 3.74 (m, 1H), 3.62 (m, 5H), 3.51 (m, 4H), 3.40 (m, 4H), 3.22 (s, 6H), 3.12 (m, 3H), 2.10–1.75 (m, 4H), 1.05–0.70 (m, 9H). MS (ESI, positive): 908.2, 930.2.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of the formula:

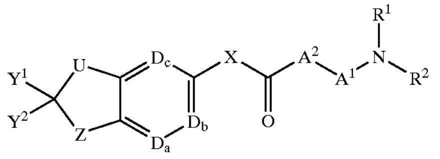

wherein $R^1$ and $R^2$ are each members independently selected from the group consisting of hydrogen, $(C_1-C_8)$alkyl, $(C_1-C_8)$heteroalkyl, aryl, heteroaryl, aryl$(C_1-C_8)$alkyl, aryl$(C_1-C_8)$heteroalkyl, heteroaryl$(C_1-C_8)$alkyl, and heteroaryl$(C_1-C_8)$heteroalkyl, with the proviso that at least one of $R^1$ and $R^2$ is selected from the group consisting of aryl, heteroaryl, aryl$(C_1-C_8)$alkyl, aryl $(C_1-C_8)$heteroalkyl, heteroaryl$(C_1-C_8)$alkyl and heteroaryl$(C_1-C_8)$heteroalkyl;

$A^1$ is a member selected from the group consisting of L-α-amino acid fragments, D-α-amino acid fragments and fragments having the formula:

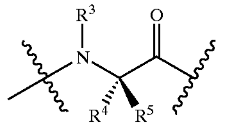

wherein $R^3$ is selected from the group consisting of hydrogen and $(C_1-C_4)$ alkyl;

$R^4$ and $R^5$ are each members independently selected from the group consisting of hydrogen, $(C_1-C_8)$alkyl and $(C_1-C_8)$ heteroalkyl, or can be individually combined with $R^3$ to form a 5-, 6-, 7- or 8-membered ring containing from one to three heteroatoms;

$A^2$ is a member selected from the group consisting of L-α-amino acid fragments, D-α-amino acid fragments and fragments having the formula:

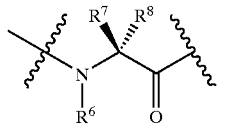

wherein $R^6$ is selected from the group consisting of hydrogen and $(C_1-C_4)$alkyl;

$R^7$ and $R^8$ are each members independently selected from the group consisting of hydrogen, $(C_1-C_8)$alkyl and $(C_1-C_8)$ heteroalkyl, or can be combined with each other to form a 5-, 6-, 7- or 8-membered ring containing from zero to three heteroatoms;

X is a member selected from the group consisting of a bond, a $(C_1-C_4)$ saturated or unsaturated alkylene linking group and a $(C_1-C_4)$ saturated or unsaturated heteroalkylene linking group;

$D_a$, $D_b$ and $D_c$ are each independently selected from the group consisting of =N— and =C($R^9$)— wherein each $R^9$ is independently selected from the group consisting of hydrogen, halogen, cyano, nitro, ($C_1$–$C_6$) alkyl, ($C_1$–$C_6$)heteroalkyl, ($C_1$–$C_6$)alkoxy, ($C_1$–$C_6$) thioalkoxy, —$NR^{10}OR^{11}$, —C(O)$OR^{10}$, —C(O)$NR^{10}OR^{11}$, —O—C(O)$OR^{10}$, —$NR^{11}$—C(O)$OR^{10}$, —$NR^{10}$—$SO_2R^{12}$, —$NR^{10}$—C(O)$R^{11}$, —$SO_2NR^{10}R^{11}$, and —OC(O)$NR^{10}OR^{11}$;

wherein each $R^{10}$ and $R^{11}$ are each independently a member selected from the group consisting of hydrogen, ($C_1$–$C_8$)alkyl and ($C_1$–$C_8$)heteroalkyl, or when attached to the same nitrogen atom can be combined with each other to form a 5-, 6-, 7- or 8-membered ring containing from zero to three heteroatoms; and each $R^{12}$ is independently a member selected from the group consisting of ($C_1$–$C_8$)alkyl, ($C_1$–$C_8$)heteroalkyl, aryl and heteroaryl;

U and Z are each independently selected from the group consisting of a single bond, —$CH_2$—, —CH(OH)—, —C(O)—, —$CH_2$O—, —$CH_2CH_2$—, —$CH_2$C(O)—, —O—, —S—,—S—$CH_2$—,—N(C(O)—($C_1$–$C_9$) alkyl)-, —N($R^{13}$)— and —N($R^{13}$)—$CH_2$—;

wherein each $R^{13}$ is a member selected from the group consisting of hydrogen, ($C_1$–$C_8$)alkyl, aryl and ($C_1$–$C_8$) heteroalkyl;

$Y^1$ and $Y^2$ are each independently selected from the group consisting of —$CO_2$H and —$CO_2R^{14}$; and $R^{14}$ is a member selected from the group consisting of ($C_1$–$C_9$)alkyl, and ($C_1$–$C_9$)heteroalkyl, or, alternatively, when $Y^1$ and $Y^2$ are each —$CO_2R^{14}$, each $R^{14}$ and the oxygen to which it is attached, join to form a 5-, 6-, 7- or 8-membered heterocyclic ring.

2. The compound of claim 1, wherein $D_a$, $D_b$ and $D_c$ are each =CH—.

3. The compound of claim 1, wherein X is a ($C_2$–$C_4$) unsaturated alkylene linking group.

4. The compound of claim 1, wherein $A^1$ is selected from the group consisting of L-α-amino acid fragments.

5. The compound of claim 1, wherein $A^2$ is selected from the group consisting of L-α-amino acid fragments.

6. The compound of claim 1, wherein $A^1$ and $A^2$ are each independently selected from the group consisting of L-α-amino acid fragments.

7. The compound of claim 1, wherein $A^1$ and $A^2$ are each independently selected from the group consisting of L-α-amino acid fragments; X is a ($C_2$–$C_4$) unsaturated alkylene linking group; and $D_a$, $D_b$ and $D_c$ are each =CH—.

8. The compound of claim 1, wherein U is selected from the group consisting of —$CH_2$— and —CH(OH)—.

9. The compound of claim 1, wherein Z is selected from the group consisting of —$CH_2$—, —O—, —NH— and —S—.

10. The compound of claim 1, wherein U is selected from the group consisting of —$CH_2$— and —CH(OH)—; and Z is selected from the group consisting of —$CH_2$—, —O—, —NH— and —S—.

11. The compound of claim 1, wherein $A^1$ and $A^2$ are each independently selected from the group consisting of natural or unnatural L-α-amino acid fragments; X is a ($C_2$–$C_4$) unsaturated alkylene linking group; $D_a$, $D_b$ and $D_c$ are each =CH—; U is selected from the group consisting of —$CH_2$— and —CH(OH)—; and Z is selected from the group consisting of —$CH_2$—, —O—, —NH— and —S—.

12. The compound of claim 11, wherein X is an unsaturated alkylene moiety selected from the group consisting of —C($CH_3$)=CH and —CH=C($CH_3$).

13. The compound of claim 1, wherein $R^1$ and $R^2$ are each members independently selected from the group consisting of ($C_1$–$C_8$)alkyl, aryl and aryl($C_1$–$C_8$)alkyl.

14. The compound of claim 11, wherein $R^1$ and $R^2$ are each members independently selected from the group consisting of($C_1$–$C_8$)alkyl, aryl and aryl($C_1$–$C_8$)alkyl.

15. The compound of claim 1, wherein $R^1$ is an optionally substituted phenyl group.

16. The compound of claim 1, wherein $R^1$ is an optionally substituted phenyl group and $R^2$ is an optionally substituted benzyl group.

17. The compound of claim 11, wherein $R^1$ is an optionally substituted phenyl group.

18. The compound of claim 11, wherein $R^1$ is an optionally substituted phenyl group and $R^2$ is an optionally substituted benzyl group.

19. The compound of claim 1, wherein $R^1$ is an optionally substituted ($C_1$–$C_8$)alkyl or ($C_1$–$C_8$)heteroalkyl group and $R^2$ is an optionally substituted phenyl or benzyl group.

20. The compound of claim 1, wherein $R^1$ is a phenyl group substituted with up to two members selected from the group consisting of —$NHCONH_2$, —C(NH)$NH_2$, —$CONH_2$, —$CH_2$NHCO-(4-nitro-2-pyrazolyl), —CONHPh, —$CH_2NH_2$, —$CH_2$NHCO—CH=CH-(3-nitrophenyl), —$CH_3$, —Cl, —Br, —I, —$CO_2$H, —$CO_2CH_3$, —$OCR^3$, —OH, —Ph, —OPh, —CON($CH_3$)$_2$, —C($CH_3$)$_3$, —$CH_2$NHAc, —CN and —$CH_2$NHCO—CH=CH-(4-pyridyl).

21. The compound of claim 11, wherein $R^1$ is an optionally substituted ($C_1$–$C_8$)alkyl or ($C_1$–$C_8$)heteroalkyl group and $R^2$ is an optionally substituted phenyl or benzyl group.

22. The compound of claim 11, wherein $R^1$ is a phenyl group substituted with up to two members selected from the group consisting of —$NHCONH_2$, —C(NH)$NH_2$, —$CONH_2$, —$CH_2$NHCO-(4-nitro-2-pyrazolyl), —CONHPh, —$CH_2NH_2$, —$CH_2$NHCO—CH=CH-(3-nitrophenyl), —$CH_3$, —Cl, —Br, —I, —$CO_2$H, —$CO_2CH_3$, —$OCH^3$, —OH, —Ph, —OPh, —CON($CH_3$)$_2$, —C($CH_3$)$_3$, —$CH_2$NHAc, —CN and —$CH_2$NHCO—CH=CH-(4-pyridyl).

23. The compound of claim 11, wherein Z is —O—; $R^1$ is a member selected from the group consisting of an optionally substituted phenyl group or an optionally substituted heteroaryl; and $R^2$ is a member selected from the group consisting of ($C_1$–$C_8$)alkyl, ($C_1$–$C_8$)heteroalkyl, aryl ($C_1$–$C_8$)alkyl, aryl($C_1$–$C_8$)heteroalkyl, heteroaryl($C_1$–$C_8$) alkyl and heteroaryl($C_1$–$C_8$)heteroalkyl.

24. The compound of claim 4, wherein $A^1$ is an L-α-amino acid fragment derived from L-tyrosine, L-serine, L-methionine, L-alanine and L-proline.

25. The compound of claim 5, wherein $A^2$ is an L-α-amino acid fragment derived from L-valine, L-leucine, L-methionine, L-lysine, L-isoleucine, L-threonine and L-tert-butylglycine.

26. The compound of claim 11, wherein $A^1$ is an L-α-amino acid fragment derived from L-tyrosine, L-serine, L-methionine, L-alanine and L-proline; and $A^2$ is an L-α-amino acid fragment derived from L-valine, L-leucine, L-methionine, L-lysine, L-isoleucine, L-threonine and L-tert-butylglycine.

27. The compound of claim 26, wherein $R^1$ and $R^2$ are each members independently selected from the group consisting of substituted or unsubstituted ($C_1$–$C_8$)alkyl, substituted or unsubstituted aryl and substituted or unsubstituted aryl($C_1$–$C_8$)alkyl.

28. The compound of claim 27, wherein $A^1$ is an L-α-amino acid fragment derived from L-alanine or L-proline; and $A^2$ is an L-α-amino acid fragment derived from L-valine, L-leucine, L-isoleucine, or L-tert-butylglycine.

29. The compound of claim 27, wherein $A^1$ is an L-α-amino acid fragment derived from L-proline; and $A^2$ is an L-α-amino acid fragment derived from L-tert-butylglycine.

30. The compound of claim 1, having the formula:

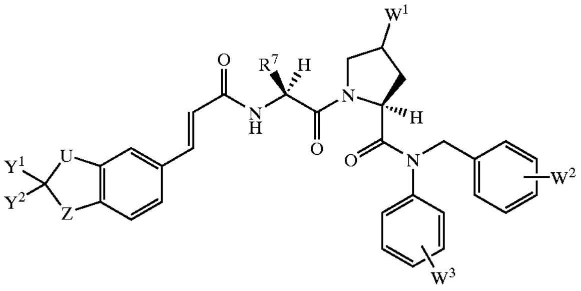

wherein $W^1$ is a member selected from the group consisting of —H, —$OR^{15}$ and —$NR^{15}R^{16}$;

$W^2$ and $W^3$ are each members independently selected from the group consisting of hydrogen, halogen, —$R^{17}$, —$CO_2R^{17}$, —$OR^{17}$, —$NR^{17}R^{18}$ and —$CONR^{17}R^{18}$;

wherein $R^{15}$, $R^{16}$, $R^{17}$ and $R^{18}$ are each members independently selected from the group consisting of hydrogen, aryl, ($C_1$–$C_8$)alkyl, ($C_1$–$C_8$)heteroalkyl, aryl ($C_1$–$C_8$)alkyl, aryl($C_1$–$C_8$)heteroalkyl, alkylsulfonyl, arylsulfonyl and arylsulfinyl;

U and Z are each members independently selected from the group consisting of —$CH_2$—, —CH(OH)—, —C(O)—, —O—, —S— and —N($R^{13}$)—.

31. The compound of claim 1, having the formula:

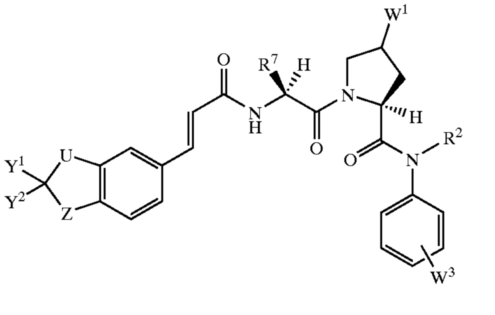

wherein $R^2$ is a member selected from the group consisting of substituted or unsubstituted ($C_1$–$C_8$)alkyl;

$W^1$ is a member selected from the group consisting of —H, —$OR^{15}$ and —$NR^{15}R^{16}$;

$W^3$ is a member selected from the group consisting of hydrogen, halogen, —$R^{17}$, —$CO_2R^{17}$, —$OR^{17}$, —$NR^{17}R^{18}$ and —$CONR^{17}R^{18}$;

wherein $R^{15}$, $R^{16}$, $R^{17}$ and $R^{18}$ are each members independently selected from the group consisting of hydrogen, aryl, ($C_1$–$C_8$)alkyl, ($C_1$–$C_8$)heteroalkyl, aryl ($C_1$–$C_8$)alkyl, aryl($C_1$–$C_8$)heteroalkyl, alkylsulfonyl, arylsulfonyl and arylsulfinyl;

U and Z are each members independently selected from the group consisting of —$CH_2$—, —CH(OH)—, —C(O)—, —O—, —S— and —N($R^{13}$)—.

32. The compound of claim 1, having the formula:

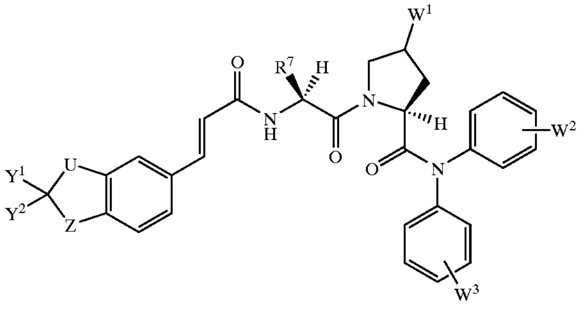

wherein $W^1$ is a member selected from the group consisting of —H, —$OR^{15}$ and $NR^{15}R^{16}$;

$W^2$ and $W^3$ are each members independently selected from the group consisting of hydrogen, halogen, —$R^{17}$, —$CO_2R^{17}$, —$OR^{17}$, —$NR^{17}R^{18}$ and —$CONR^{17}R^{18}$;

wherein $R^{15}$, $R^{16}$, $R^{17}$ and $R^{18}$ are each members independently selected from the group consisting of hydrogen, aryl, ($C_1$–$C_8$)alkyl, ($C_1$–$C_8$)heteroalkyl, aryl ($C_1$–$C_8$)alkyl, aryl($C_1$–$C_8$)heteroalkyl, alkylsulfonyl, arylsulfonyl and arylsulfinyl;

U and Z are each members independently selected from the group consisting of —$CH_2$—, —CH(OH)—, —C(O)—, —O—, —S— and —N($R^{13}$)—.

33. A composition comprising a pharmaceutically acceptable excipient and a compound having the formula:

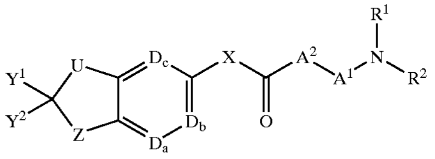

wherein $R^1$ and $R^2$ are each members independently selected from the group consisting of hydrogen, ($C_1$–$C_8$)alkyl, ($C_1$–$C_8$)heteroalkyl, aryl, heteroaryl, aryl($C_1$–$C_8$)alkyl, aryl($C_1$–$C_8$)heteroalkyl, heteroaryl($C_1$–$C_8$)alkyl, and heteroaryl($C_1$–$C_8$)heteroalkyl, with the proviso that at least one of $R^1$ and $R^2$ is selected from the group consisting of aryl, heteroaryl, aryl($C_1$–$C_8$)alkyl, aryl ($C_1$–$C_8$)heteroalkyl, heteroaryl($C_1$–$C_8$)alkyl and heteroaryl($C_1$–$C_8$)heteroalkyl;

$A^1$ is a member selected from the group consisting of L-α-amino acid fragments, D-α-amino acid fragments and fragments having the formula:

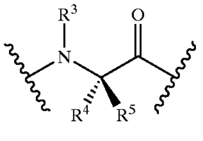

wherein $R^3$ is selected from the group consisting of hydrogen and ($C_1$–$C_4$) alkyl;

$R^4$ and $R^5$ are each members independently selected from the group consisting of hydrogen, $(C_1-C_8)$alkyl and $(C_1-C_8)$heteroalkyl, or can be individually combined with $R^3$ to form a 5-, 6-, 7- or 8-membered ring containing from one to three heteroatoms;

$A^2$ is a member selected from the group consisting of L-α-amino acid fragments, D-α-amino acid fragments and fragments having the formula:

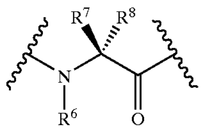

wherein $R^6$ is selected from the group consisting of hydrogen and $(C_1-C_4)$alkyl;

$R^7$ and $R^8$ are each members independently selected from the group consisting of hydrogen, $(C_1-C_8)$alkyl and $(C_1-C_8)$heteroalkyl, or can be combined with each other to form a 5-, 6-, 7- or 8-membered ring containing from zero to three heteroatoms;

X is a member selected from the group consisting of a bond, a $(C_1-C_4)$ saturated or unsaturated alkylene linking group and a $(C_1-C_4)$ saturated or unsaturated heteroalkylene linking group;

$D_a$, $D_b$ and $D_c$ are each independently selected from the group consisting of =N— and =C($R^9$)— wherein each $R^9$ is independently selected from the group consisting of hydrogen, halogen, cyano, nitro, $(C_1-C_6)$alkyl, $(C_1-C_6)$heteroalkyl, $(C_1-C_6)$alkoxy, $(C_1-C_6)$thioalkoxy, —$NR^{10}R^{11}$, —C(O)$OR^{10}$, —C(O)$NR^{10}R^{11}$, —O—C(O)$OR^{10}$, —$NR^{11}$—C(O)$OR^{10}$, —$NR^{10}$—$SO_2R^{12}$, —$NR^{10}$—C(O)$R^{11}$, —$SO_2NR^{10}R^{11}$, and —OC(O)$NR^{10}R^{11}$;

wherein each $R^{10}$ and $R^{11}$ are each independently a member selected from the group consisting of hydrogen, $(C_1-C_8)$alkyl and $(C_1-C_8)$heteroalkyl, or when attached to the same nitrogen atom can be combined with each other to form a 5-, 6-, 7- or 8-membered ring containing from zero to three heteroatoms; and each $R^{12}$ is independently a member selected from the group consisting of $(C_1-C_8)$alkyl, $(C_1-C_8)$heteroalkyl, aryl and heteroaryl;

U and Z are each independently selected from the group consisting of a single bond, —$CH_2$—, —CH(OH)—, —C(O)—, —$CH_2$O—, —$CH_2CH_2$—, —$CH_2$C(O)—, —O—, —S—, —S—$CH_2$—, —N(C(O)—$(C_1-C_9)$alkyl)-, —N($R^{13}$)— and —N($R^{13}$)—$CH_2$—;

wherein $R^{13}$ is a member selected from the group consisting of H, $(C_1-C_8)$alkyl, aryl and $(C_1-C_8)$heteroalkyl;

$Y^1$ and $Y^2$ are each independently selected from the group consisting of —$CO_2H$ and —$CO_2R^{14}$ wherein $R^{14}$ is a member selected from the group consisting of $(C_1-C_9)$alkyl, $(C_1-C_9)$heteroalkyl, or, alternatively, when $Y^1$ and $Y^2$ are each —$CO_2R^{14}$, each $R^{14}$ and the oxygen to which it is attached, join to form a 5-, 6-, 7-, or 8-membered heterocyclic ring.

34. The composition of claim 33, wherein $D_a$, $D_b$ and $D_c$ are each =CH—.

35. The composition of claim 33, wherein X is a $(C_2-C_4)$ unsaturated alkylene linking group.

36. The composition of claim 33, wherein $A^1$ is selected from the group consisting of L-α-amino acid fragments.

37. The composition of claim 33, wherein $A^2$ is selected from the group consisting of L-α-amino acid fragments.

38. The composition of claim 33, wherein $A^1$ and $A^2$ are each independently selected from the group consisting of L-α-amino acid fragments.

39. The composition of claim 33, wherein $A^1$ and $A^2$ are each independently selected from the group consisting of L-α-amino acid fragments; X is a $(C_2-C_4)$ unsaturated alkylene linking group; and $D_a$, $D_b$ and $D_c$ are each =CH—.

40. The composition of claim 33, wherein U is selected from the group consisting of —$CH_2$— and —CH(OH)—.

41. The composition of claim 33, wherein Z is selected from the group consisting of —$CH_2$—, —O—, —NH— and —S—.

42. The composition of claim 33, wherein U is selected from the group consisting of —$CH_2$— and —CH(OH)—; and Z is selected from the group consisting of —$CH_2$—, —O—, —NH— and —S—.

43. The composition of claim 33, wherein $A^1$ and $A^2$ are each independently selected from the group consisting of natural or unnatural L-α-amino acid fragments; X is a $(C_2-C_4)$ unsaturated alkylene linking group; $D_a$, $D_b$ and $D_c$ are each =CH—; U is selected from the group consisting of —$CH_2$— and —CH(OH)—; and Z is selected from the group consisting of —$CH_2$—, —O—, —NH— and —S—.

44. The composition of claim 43, wherein X is an unsaturated alkylene moiety selected from the group consisting of —C($CH_3$)=CH and —CH=C($CH_3$).

45. The composition of claim 33, wherein $R^1$ and $R^2$ are each members independently selected from the group consisting of $(C_1-C_8)$alkyl, aryl and aryl$(C_1-C_8)$alkyl.

46. The composition of claim 43, wherein $R^1$ and $R^2$ are each members independently selected from the group consisting of $(C_1-C_8)$alkyl, aryl and aryl$(C_1-C_8)$alkyl.

47. The composition of claim 33, wherein $R^1$ is an optionally substituted phenyl group.

48. The composition of claim 33, wherein $R^1$ is an optionally substituted phenyl group and $R^2$is an optionally substituted benzyl group.

49. The composition of claim 43, wherein $R^1$ is an optionally substituted phenyl group.

50. The composition of claim 43, wherein $R^1$ is an optionally substituted phenyl group and $R^2$ is an optionally substituted benzyl group.

51. The composition of claim 33, wherein $R^1$ is an optionally substituted $(C_1-C_8)$alkyl or $(C_1-C_8)$heteroalkyl group and $R^2$ is an optionally substituted phenyl or benzyl group.

52. The composition of claim 33, wherein $R^1$ is a phenyl group substituted with up to two members selected from the group consisting of —$NHCONH_2$, —C(NH)$NH_2$, —$CONH_2$, —$CH_2$NHCO-(4-nitro-2-pyrazolyl), —CONHPh, —$CH_2NH_2$, —$CH_2$NHCO—CH=CH-(3-nitrophenyl), —$CH_3$, —Cl, —Br, —I, —$CO_2H$, —$CO_2CH_3$, —$OCH_3$, —OH, —Ph, —OPh, —CON$(CH_3)_2$, —C$(CH_3)_3$, —$CH_2$NHAc, —CN and —$CH_2$NHCO—CH=CH-(4-pyridyl).

53. The composition of claim 43, wherein $R^1$ is an optionally substituted $(C_1-C_8)$alkyl or $(C_1-C_8)$heteroalkyl group and $R^2$ is an optionally substituted phenyl or benzyl group.

54. The composition of claim 43, wherein $R^1$ is a phenyl group substituted with up to two members selected from the group consisting of —$NHCONH_2$, —C(NH)$NH_2$, —$CONH_2$, —$CH_2NHCO$-(4-nitro-2-pyrazolyl), —CONHPh, —$CH_2NH_2$, —$CH_2NHCO$—CH═CH-(3-nitrophenyl), —$CH_3$, —Cl, —Br, —I, —$CO_2H$, —$CO_2CH_3$, —$OCH_3$, —OH, —Ph, —OPh, —CON$(CH_3)_2$, —C$(CH_3)_3$, —$CH_2NHAc$, —CN and —$CH_2NHCO$—CH═CH-(4-pyridyl).

55. The composition of claim 43, wherein Z is —O—; $R^1$ is a member selected from the group consisting of an optionally substituted phenyl group or an optionally substituted heteroaryl; and $R^2$ is a member selected from the group consisting of ($C_1$–$C_8$)alkyl, ($C_1$–$C_8$)heteroalkyl, aryl($C_1$–$C_8$)alkyl, aryl($C_1$–$C_8$)heteroalkyl, heteroaryl($C_1$–$C_8$) alkyl and heteroaryl($C_1$–$C_8$)heteroalkyl.

56. The composition of claim 36, wherein $A^1$ is an L-α-amino acid fragment derived from L-tyrosine, L-serine, L-methionine, L-alanine and L-proline.

57. The composition of claim 37, wherein $A^2$ is an L-α-amino acid fragment derived from L-valine, L-leucine, L-methionine, L-lysine, L-isoleucine, L-threonine and L-tert-butylglycine.

58. The composition of claim 43, wherein $A^1$ is an L-α-amino acid fragment derived from L-tyrosine, L-serine, L-methionine, L-alanine and L-proline; and $A^2$ is an L-α-amino acid fragment derived from L-valine, L-leucine, L-methionine, L-lysine, L-isoleucine, L-threonine and L-tert-butylglycine.

59. The composition of claim 58, wherein $R^1$ and $R^2$ are each members independently selected from the group consisting of substituted or unsubstituted ($C_1$–$C_8$)alkyl, substituted or unsubstituted aryl and substituted or unsubstituted aryl($C_1$–$C_8$)alkyl.

60. The composition of claim 59, wherein $A^1$ is an L-α-amino acid fragment derived from L-alanine or L-proline; and $A^2$ is an L-α-amino acid fragment derived from L-valine, L-leucine, L-isoleucine, or L-tert-butylglycine.

61. The composition of claim 59, wherein $A^1$ is an L-α-amino acid fragment derived from L-proline; and $A^2$ is an L-α-amino acid fragment derived from L-tert-butylglycine.

62. The composition of claim 33, said compound having the formula:

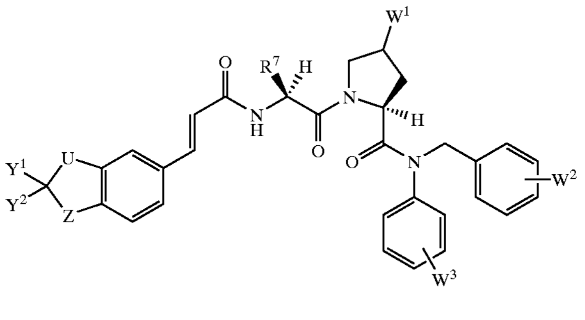

wherein $W^1$ is a member selected from the group consisting of —H, —$OR^{15}$ and —$NR^{15}R^{16}$;

$W^2$ and $W^3$ are each members independently selected from the group consisting of hydrogen, halogen, —$R^{17}$, —$CO_2R^{17}$, —$OR^{17}$, —$NR^{17}R^{18}$ and —$CONR^{17}R^{18}$;

wherein $R^{15}$, $R^{16}$, $R^{17}$ and $R^{18}$ are each members independently selected from the group consisting of hydrogen, aryl, ($C_1$–$C_8$)alkyl, ($C_1$–$C_8$)heteroalkyl, aryl($C_1$–$C_8$)alkyl, aryl($C_1$–$C_8$)heteroalkyl, alkylsulfonyl, arylsulfonyl and arylsulfinyl;

U and Z are each members independently selected from the group consisting of —$CH_2$—, —CH(OH)—, —C(O)—, —O—, —S— and —N($R^{13}$)—.

63. The composition of claim 33, said compound having the formula:

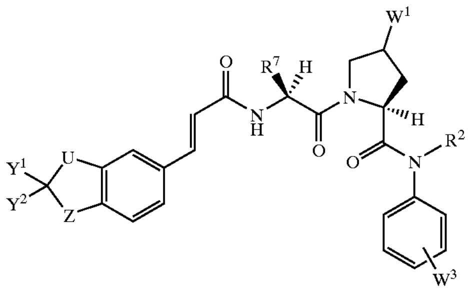

wherein $R^2$ is a member selected from the group consisting of unsubstituted ($C_1$–$C_8$)alkyl;

$W^1$ is a member selected from the group consisting of —H, —$OR^{15}$ and —$NR^{15}R^{16}$;

$W^3$ is a member selected from the group consisting of hydrogen, halogen, —$R^{17}$, —$CO_2R^{17}$, —$OR^{17}$, —$NR^{17}R^{18}$ and —$CONR^{17}R^{18}$;

wherein $R^{15}$, $R^{16}$, $R^{17}$ and $R^{18}$ are each members independently selected from the group consisting of hydrogen, aryl, ($C_1$–$C_8$)alkyl, ($C_1$–$C_8$)heteroalkyl, aryl($C_1$–$C_8$)alkyl, aryl($C_1$–$C_8$)heteroalkyl, alkylsulfonyl, arylsulfonyl and arylsulfinyl;

U and Z are each members independently selected from the group consisting of —$CH_2$—, —CH(OH)—, —C(O)—, —O—, —S— and —N($R^{13}$)—.

64. The composition of claim 33, said compound having the formula:

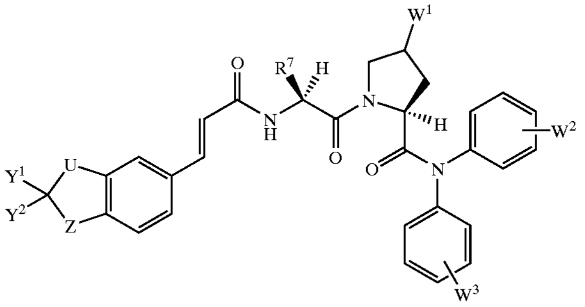

wherein $W^1$ is a member selected from the group consisting of —H, —$OR^{15}$ and —$NR^{15}R^{16}$;

$W^2$ and $W^3$ are each members independently selected from the group consisting of hydrogen, halogen, —$R^{17}$, —$CO_2R^{17}$, —$OR^{17}$, —$NR^{17}R^{18}$ and —$CONR_{17}R^{18}$;

wherein $R^{15}$, $R^{16}$, $R^{17}$ and $R^{18}$ are each members independently selected from the group consisting of hydrogen, aryl, ($C_1$—$C_8$)alkyl, ($C_1$——$C_8$)heteroalkyl, aryl($C_1$–$C_8$)alkyl, aryl($C_1$–$C_8$)heteroalkyl, alkylsulfonyl, arylsulfonyl and arylsulfinyl;

U and Z are each members independently selected from the group consisting of —$CH_2$—, —CH(OH)—, —C(O)—, —O—, —S— and —N($R^{13}$)—.

65. A method for treating asthma in a host in need thereof, comprising administering to said host a therapeutically effective amount of compound of the formula:

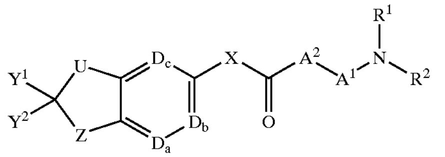

wherein $R^1$ and $R^2$ are each members independently selected from the group consisting of hydrogen, $(C_1-C_8)$alkyl, $(C_1-C_8)$heteroalkyl, aryl, heteroaryl, aryl$(C_1-C_8)$alkyl, aryl$(C_1-C_8)$heteroalkyl, heteroaryl$(C_1-C_8)$alkyl, and heteroaryl$(C_1-C_8)$heteroalkyl, with the proviso that at least one of $R^1$ and $R^2$ is selected from the group consisting of aryl, heteroaryl, aryl$(C_1-C_8)$alkyl, aryl $(C_1-C_8)$heteroalkyl, heteroaryl$(C_1-C_8)$alkyl and heteroaryl$(C_1-C_8)$heteroalkyl;

$A^1$ is a member selected from the group consisting of L-α-amino acid fragments, D-α-amino acid fragments and fragments having the formula:

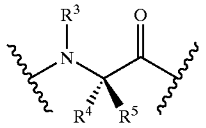

wherein $R^3$ is selected from the group consisting of hydrogen and $(C_1-C_4)$ alkyl;

$R^4$ and $R^5$ are each members independently selected from the group consisting of hydrogen, $(C_1-C_8)$alkyl and $(C_1-C_8)$ heteroalkyl, or can be individually combined with $R^3$ to form a 5-, 6-, 7- or 8-membered ring containing from one to three heteroatoms;

$A^2$ is a member selected from the group consisting of L-α-amino acid fragments, D-α-amino acid fragments and fragments having the formula:

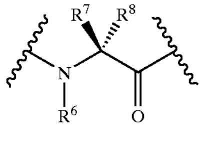

wherein $R^6$ is selected from the group consisting of hydrogen and $(C_1-C_4)$alkyl;

$R^7$ and $R^8$ are each members independently selected from the group consisting of hydrogen, $(C_1-C_8)$alkyl and $(C_1-C_8)$ heteroalkyl, or can be combined with each other to form a 5-, 6-, 7- or 8-membered ring containing from zero to three heteroatoms;

X is a member selected from the group consisting of a bond, a $(C_1-C_4)$ saturated or unsaturated alkylene linking group and a $(C_1-C_4)$ saturated or unsaturated heteroalkylene linking group;

$D_a$, $D_b$ and $D_c$ are each independently selected from the group consisting of $=N-$ and $=C(R^9)-$ wherein each $R^9$ is independently selected from the group consisting of hydrogen, halogen, cyano, nitro, $(C_1-C_6)$ alkyl, $(C_1-C_6)$heteroalkyl, $(C_1-C_6)$alkoxy, $(C_1-C_6)$ thioalkoxy, $-NR^{10}R^{11}$, $-C(O)OR^{10}$, $-C(O)NR^{10}R^{11}$, $-O-C(O)OR^{10}$, $-NR^{11}-C(O)OR^{10}$, $-NR^{10}-SO_2R^{12}$, $-NR^{10}-C(O)R^{11}$, $-SO_2NR^{10}R^{11}$, and $-OC(O)NR^{10}R^{11}$;

wherein each $R^{10}$ and $R^{11}$ are each independently a member selected from the group consisting of hydrogen, $(C_1-C_8)$alkyl and $(C_1-C_8)$heteroalkyl, or when attached to the same nitrogen atom can be combined with each other to form a 5-, 6-, 7- or 8-membered ring containing from zero to three heteroatoms; and each $R^{12}$ is independently a member selected from the group consisting of $(C_1-C_8)$alkyl, $(C_1-C_8)$heteroalkyl, aryl and heteroaryl;

U and Z are each independently selected from the group consisting of a single bond, $-CH_2-$, $-CH(OH)-$, $-C(O)-$, $-CH_2O-$, $-CH_2CH_2-$, $-CH_2C(O)-$, $-O-$, $-S-$, $-S-CH_2-$, $-N(C(O)-(C_1-C_9)$ alkyl)-, $-N(R^{13})-$ and $-N(R^{13})-CH_2-$;

wherein $R^{13}$ is a member selected from the group consisting of hydrogen, $(C_1-C_8)$alkyl, aryl and $(C_1-C_8)$heteroalkyl;

$Y^1$ and $Y^2$ are each independently selected from the group consisting of $-CO_2H$ and $-CO_2R^{14}$; and $R^{14}$ is a member selected from the group consisting of $(C_1-C_9)$alkyl, $(C_1-C_9)$heteroalkyl, or, alternatively, when $Y^1$ and $Y^2$ are each $-CO_2R^{14}$, each $R^{14}$ and the oxygen to which it is attached, join to form a 5-, 6-, 7-, or 8-membered heterocyclic ring.

66. The method of claim 65, wherein $D_a$, $D_b$ and $D_c$ are each $=CH-$.

67. The method of claim 65, wherein X is a $(C_2-C_4)$ unsaturated alkylene linking group.

68. The method of claim 65, wherein $A^1$ is selected from the group consisting of L-α-amino acid fragments.

69. The method of claim 65, wherein $A^2$ is selected from the group consisting of L-α-amino acid fragments.

70. The method of claim 65, wherein $A^1$ and $A^2$ are each independently selected from the group consisting of L-α-amino acid fragments.

71. The method of claim 65, wherein $A^1$ and $A^2$ are each independently selected from the group consisting of L-α-amino acid fragments; X is a $(C_2-C_4)$ unsaturated alkylene linking group; and $D_a$, $D_b$ and $D_c$ are each $=CH-$.

72. The method of claim 65, wherein U is selected from the group consisting of $-CH_2-$ and $-CH(OH)-$.

73. The method of claim 65, wherein Z is selected from the group consisting of $-CH_2-$, $-O-$, $-NH$ and $-S-$.

74. The method of claim 65, wherein U is selected from the group consisting of $-CH_2-$ and $-CH(OH)-$; and Z is selected from the group consisting of $-CH_2-$, $-O-$, $-NH-$ and $-S-$.

75. The method of claim 65, wherein $A^1$ and $A^2$ are each independently selected from the group consisting of natural or unnatural L-α-amino acid fragments; X is a $(C_2-C_4)$ unsaturated alkylene linking group; $D_a$, $D_b$ and $D_c$ are each $=CH-$; U is selected from the group consisting of $-CH_2-$ and $-CH(OH)-$; and Z is selected from the group consisting of $-CH_2-$, $-O-$, $-NH-$ and $-S-$.

76. The method of claim 75, wherein X is an unsaturated alkylene moiety selected from the group consisting of $-C(CH_3)=CH$ and $-CH=C(CH_3)$.

77. The method of claim 65, wherein $R^1$ and $R^2$ are each members independently selected from the group consisting of $(C_1-C_8)$alkyl, aryl and aryl$(C_1-C_8)$alkyl.

78. The method of claim 75, wherein $R^1$ and $R^2$ are each members independently selected from the group consisting of $(C_1-C_8)$alkyl, aryl and aryl$(C_1-C_8)$alkyl.

79. The method of claim 65, wherein $R^1$ is an optionally substituted phenyl group.

80. The method of claim 65, wherein $R^1$ is an optionally substituted phenyl group and $R^2$ is an optionally substituted benzyl group.

81. The method of claim 75, wherein $R^1$ is an optionally substituted phenyl group.

82. The method of claim 75, wherein $R^1$ is an optionally substituted phenyl group and $R^2$ is an optionally substituted benzyl group.

83. The method of claim 65, wherein $R^1$ is an optionally substituted $(C_1-C_8)$alkyl or $(C_1-C_8)$heteroalkyl group and $R^2$ is an optionally substituted phenyl or benzyl group.

84. The method of claim 65, wherein $R^1$ is a phenyl group substituted with up to two members selected from the group consisting of —$NHCONH_2$, —$C(NH)NH_2$, —$CONH_2$, —$CH_2NHCO$-(4-nitro-2-pyrazolyl), —CONHPh, —$CH_2NH_2$, —$CH_2NHCO$—CH═CH-(3-nitrophenyl), —$CH_3$, —Cl, —Br, —I, —$CO_2H$, —$CO_2CH_3$, —$OCH_3$, —OH, —Ph, —OPh, —$CON(CH_3)_2$, —$C(CH_3)_3$, —$CH_2NHAc$, —CN and —$CH_2NHCO$—CH═CH-(4-pyridyl).

85. The method of claim 75, wherein $R^1$ is an optionally substituted $(C_1-C_8)$alkyl or $(C_1-C_8)$heteroalkyl group and $R^2$ is an optionally substituted phenyl or benzyl group.

86. The method of claim 75, wherein $R^1$ is a phenyl group substituted with up to two members selected from the group consisting of —$NHCONH_2$, —$C(NH)NH_2$, —$CONH_2$, —$CH_2NHCO$-(4-nitro-2-pyrazolyl), —CONHPh, —$CH_2NH_2$, —$CH_2NHCO$—CH═CH-(3-nitrophenyl), —$CH_3$, —Cl, —Br, —I, —$CO_2H$, —$CO_2CH_3$, —$OCH_3$, —OH, —Ph, —OPh, —$CON(CH_3)_2$, —$C(CH_3)_3$, —$CH_2NHAc$, —CN and —$CH_2NHCO$—CH═CH-(4-pyridyl).

87. The method of claim 75, wherein Z is —O—; $R^1$ is a member selected from the group consisting of an optionally substituted phenyl group or an optionally substituted heteroaryl; and $R^2$ is a member selected from the group consisting of $(C_1-C_8)$alkyl, $(C_1-C_8)$heteroalkyl, aryl $(C_1-C_8)$alkyl, aryl$(C_1-C_8)$heteroalkyl, heteroaryl$(C_1-C_8)$ alkyl and heteroaryl$(C_1-C_8)$heteroalkyl.

88. The method of claim 68, wherein $A^1$ is an L-α-amino acid fragment derived from L-tyrosine, L-serine, L-methionine, L-alanine and L-proline.

89. The method of claim 69, wherein $A^2$ is an L-α-amino acid fragment derived from L-valine, L-leucine, L-methionine, L-lysine, L-isoleucine, L-threonine and L-tert-butylglycine.

90. The method of claim 75, wherein $A^1$ is an L-α-amino acid fragment derived from L-tyrosine, L-serine, L-methionine, L-alanine and L-proline; and $A^2$ is an L-αt-amino acid fragment derived from L-valine, L-leucine, L-methionine, L-lysine, L-isoleucine, L-threonine and L-tert-butylglycine.

91. The method of claim 90, wherein $R^1$ and $R^2$ are each members independently selected from the group consisting of substituted or unsubstituted $(C_1-C_8)$alkyl, substituted or unsubstituted aryl and substituted or unsubstituted aryl $(C_1-C_8)$alkyl.

92. The method of claim 91, wherein $A^1$ is an L-α-amino acid fragment derived from L-alanine or L-proline; and $A^2$ is an L-α-amino acid fragment derived from L-valine, L-leucine, L-isoleucine, or L-tert-butylglycine.

93. The method of claim 91, wherein $A^1$ is an L-α-amino acid fragment derived from L-proline; and $A^2$ is an L-α-amino acid fragment derived from L-tert-butylglycine.

94. The method of claim 65, wherein said compound has the formula:

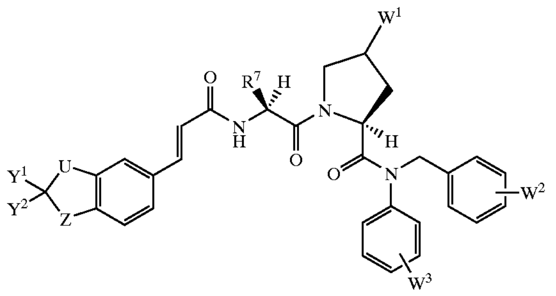

wherein $W^1$ is a member selected from the group consisting of —H, —$OR^{15}$ and —$NR^{15}R^{16}$;

$W^2$ and $W^3$ are each members independently selected from the group consisting of hydrogen, halogen, —$R^{17}$, —$CO_2R^{17}$, —$OR^{17}$, —$NR^{17}R^{18}$ and —$CONR^{17}R^{18}$;

wherein $R^{15}$, $R^{16}$, $R^{17}$ and $R^{18}$ are each members independently selected from the group consisting of hydrogen, aryl, $(C_1-C_8)$alkyl, $(C_1-C_8)$heteroalkyl, aryl $(C_1-C_8)$alkyl, aryl$(C_1-C_8)$heteroalkyl, alkylsulfonyl, arylsulfonyl and arylsulfinyl;

U and Z are each members independently selected from the group consisting of —$CH_2$—, —CH(OH)—, —C(O)—, —O—, —S— and —$N(R^{13})$—.

95. The method of claim 65, wherein said compound has the formula:

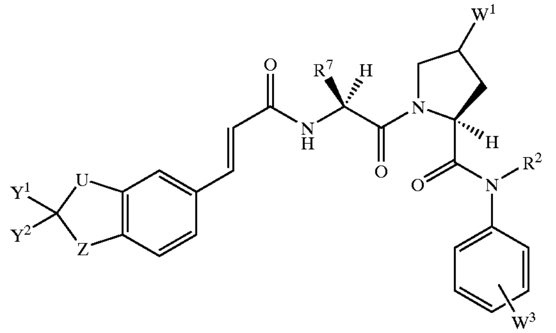

wherein $R^2$ is a member selected from the group consisting of substituted or unsubstituted $(C_1-C_8)$alkyl;

$W^1$ is a member selected from the group consisting of —H, —$OR^{15}$ and —$NR^{15}R^{16}$;

$W^3$ is a member selected from the group consisting of hydrogen, halogen, —$R^{17}$, —$CO_2R^{17}$, —$OR^{17}$, —$NR^{17}R^{18}$ and —$CONR^{17}R^{18}$;

wherein $R^{15}$, $R^{16}$, $R^{17}$ and $R^{18}$ are each members independently selected from the group consisting of hydrogen, aryl, $(C_1-C_8)$alkyl, $(C_1-C_8)$heteroalkyl, aryl $(C_1-C_8)$alkyl, aryl$(C_1-C_8)$heteroalkyl, alkylsulfonyl, arylsulfonyl and arylsulfinyl;

U and Z are each members independently selected from the group consisting of —$CH_2$—, —CH(OH)—, —C(O)—, —O—, —S— and —$N(R^{13})$—.

96. The method of claim 65, wherein said compound has the formula:

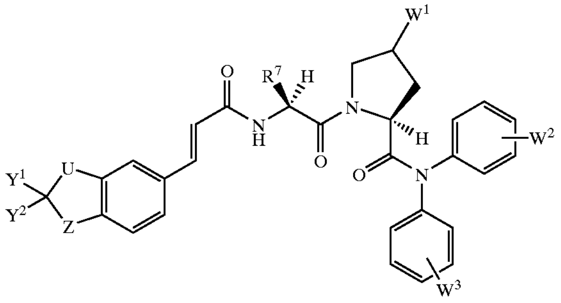

wherein $W^1$ is a member selected from the group consisting of —H, —$OR^{15}$ and —$NR^{15}R^{16}$;

$W^2$ and $W^3$ are each members independently selected from the group consisting of hydrogen, halogen, —$R^{17}$, —$CO_2R^{17}$, —$OR^{17}$, —$NR^{17}R^{18}$ and —$CONR^{17}R^{18}$;

wherein $R^{15}$, $R^{16}$, $R^{17}$ and $R^{18}$ are each members independently selected from the group consisting of hydrogen, aryl, $(C_1–C_8)$alkyl, $(C_1–C_8)$heteroalkyl, aryl $(C_1–C_8)$alkyl, aryl$(C_1–C_8)$heteroalkyl, alkylsulfonyl, arylsulfonyl and arylsulfinyl;

U and Z are each members independently selected from the group consisting of —$CH_2$—, —CH(OH)—, —C(O)—, —O—, —S— and —$N(R^{13})$—.

97. The method in accordance with claim 65, wherein said compound of said formula is administered in combination with a second therapeutic agent.

98. The method in accordance with claim 97, wherein said second therapeutic agent is selected from the group consisting of loratadine, fluticasone propionate, beclametasone dipróprionate, budesonide, salmeterol xinafoate, ipratropium bromide, fexofenadine hydrochloride, cetirizine dihydrochloride, triamcinolone acetonide, cromolyn, salbutamol, montelukast sodium, ketotifen hydrogen fumarate, formoterol, zafirlukast, momefasone furoate, azelastine hydrochloride, epinastine, seratrodast, captropril, ramipril, zofenopril, colchicine, enalapril, lisinopril, trandolapril, gold sodium thiomalate, calcipotriene, cyclosporine, vinbiastine and dapsone.

99. The method in accordance with claim 97, wherein said compound of claim 1 and said second therapeutic agent are administered sequentially.

100. The method in accordance with claim 97, wherein said compound of claim 1 and said second therapeutic agent are administered concurrently.

101. A method in accordance with claim 97, wherein said compound of claim 1 and said second therapeutic agent are each administered at dosages of from 1/100 to ½ of their dosages when administered individually.

102. A method in accordance with claim 97, wherein said compound of claim 1 and said second therapeutic agent are each administered at dosages of from 1/10 to ¼ of their dosages when administered individually.

* * * * *